United States Patent
Ruiz Ortiz et al.

(10) Patent No.: US 10,813,662 B2
(45) Date of Patent: Oct. 27, 2020

(54) ACOUSTIC DRIVETRAIN WITH EXTERNAL COLLAR AT NODAL POSITION

(71) Applicant: ETHICON LLC, Guaynabo, PR (US)

(72) Inventors: Rafael J. Ruiz Ortiz, Mason, OH (US); Craig T. Davis, Cincinnati, OH (US); Stephen M. Leuck, Cincinnati, OH (US); Benjamin M. Boyd, Fairborn, OH (US); Joseph Dennis, Cincinnati, OH (US); Joseph E. Hollo, Liberty Township, OH (US); Nathan Cummings, Blue Ash, OH (US); Ion V. Nicolaescu, Carpentersville, IL (US); Tony C. Siebel, Cincinnati, OH (US); Joseph Isosaki, Cincinnati, OH (US); Frederick L. Estera, Cincinnati, OH (US); John E. Brady, Liberty Township, OH (US); Bryce L. Heitman, Cincinnati, OH (US); Cory G. Kimball, Hamilton, OH (US)

(73) Assignee: Ethicon LLC, Guaynabo, PR (US)

(*) Notice: Subject to any disclaimer, the term of this patent is extended or adjusted under 35 U.S.C. 154(b) by 427 days.

(21) Appl. No.: 15/644,930

(22) Filed: Jul. 10, 2017

(65) Prior Publication Data
US 2019/0008546 A1    Jan. 10, 2019

(51) Int. Cl.
*A61B 17/32*    (2006.01)
*A61B 18/00*    (2006.01)
(Continued)

(52) U.S. Cl.
CPC .......... *A61B 17/320092* (2013.01); *A61B 2017/00367* (2013.01); *A61B 2017/00477* (2013.01);
(Continued)

(58) Field of Classification Search
CPC .... A61B 17/320092; A61B 2017/2929; A61B 2017/00367; A61B 2017/00477;
(Continued)

(56) References Cited

U.S. PATENT DOCUMENTS 5,059,210 A    10/1991   Clark et al.
5,322,055 A     6/1994   Davison et al.
(Continued)

OTHER PUBLICATIONS

U.S. Appl. No. 15/644,944, filed Jul. 10, 2017.

*Primary Examiner* — Anh T Dang
(74) *Attorney, Agent, or Firm* — Frost Brown Todd LLC

(57) ABSTRACT

An ultrasonic surgical instrument includes a body, a shaft, an ultrasonic transducer, a waveguide, and an end effector coupled to a distal end of the shaft. A rotation knob is rotatably coupled to the body and is configured to rotate the shaft, the waveguide, and the end effector together relative to the body. A torque transfer structure is positioned radially outwardly of and in direct contact with the waveguide at an acoustic node thereof. The torque transfer structure is rotationally fixed relative to the waveguide and is configured to rotationally couple the waveguide with the shaft and the rotation knob. The waveguide includes a first axial constraining feature defining a distally facing surface, and the torque transfer structure includes a second axial constraining feature defining a proximally facing surface configured to abut the distally facing surface to constrain the waveguide axially relative to the torque transfer structure and the body.

14 Claims, 27 Drawing Sheets

(51) Int. Cl.
*A61B 17/00* (2006.01)
*A61B 17/29* (2006.01)

(52) U.S. Cl.
CPC .............. *A61B 2017/2929* (2013.01); *A61B 2017/320071* (2017.08); *A61B 2017/320093* (2017.08); *A61B 2017/320095* (2017.08); *A61B 2017/320098* (2017.08)

(58) Field of Classification Search
CPC ....... A61B 2017/320093; A61B 2017/320071; A61B 2017/320098; A61B 2017/320095
See application file for complete search history.

(56) References Cited

U.S. PATENT DOCUMENTS

| | | | |
|---|---|---|---|
| 5,792,135 A | 8/1998 | Madhani et al. | |
| 5,817,084 A | 10/1998 | Jensen | |
| 5,873,873 A | 2/1999 | Smith et al. | |
| 5,878,193 A | 3/1999 | Wang et al. | |
| 5,980,510 A | 11/1999 | Tsonton et al. | |
| 6,221,029 B1 * | 4/2001 | Mathis | A61B 10/0233 600/564 |
| 6,231,565 B1 | 5/2001 | Tovey et al. | |
| 6,283,981 B1 | 9/2001 | Beaupre | |
| 6,309,400 B2 | 10/2001 | Beaupre | |
| 6,325,811 B1 | 12/2001 | Messerly | |
| 6,364,888 B1 | 4/2002 | Niemeyer et al. | |
| 6,423,082 B1 | 7/2002 | Houser et al. | |
| 6,773,444 B2 | 8/2004 | Messerly | |
| 6,783,524 B2 | 8/2004 | Anderson et al. | |
| 7,524,320 B2 | 4/2009 | Tierney et al. | |
| 7,691,098 B2 | 4/2010 | Wallace et al. | |
| 7,806,891 B2 | 10/2010 | Nowlin et al. | |
| 8,057,498 B2 | 11/2011 | Robertson | |
| 8,461,744 B2 | 6/2013 | Wiener et al. | |
| 8,479,969 B2 | 7/2013 | Shelton, IV | |
| 8,497,436 B2 | 7/2013 | Palmer et al. | |
| 8,502,091 B2 | 8/2013 | Palmer et al. | |
| 8,573,461 B2 | 11/2013 | Shelton, IV et al. | |
| 8,573,465 B2 | 11/2013 | Shelton, IV | |
| 8,591,536 B2 | 11/2013 | Robertson | |
| 8,602,288 B2 | 12/2013 | Shelton, IV et al. | |
| 8,616,431 B2 | 12/2013 | Timm et al. | |
| 8,623,027 B2 | 1/2014 | Price et al. | |
| 8,663,220 B2 | 3/2014 | Wiener et al. | |
| 8,783,541 B2 | 7/2014 | Shelton, IV et al. | |
| 8,800,838 B2 | 8/2014 | Shelton, IV | |
| 8,820,605 B2 | 9/2014 | Shelton, IV | |
| 8,844,789 B2 | 9/2014 | Shelton, IV et al. | |
| 9,017,355 B2 | 4/2015 | Smith et al. | |
| 9,095,367 B2 | 8/2015 | Olson et al. | |
| 9,301,759 B2 | 4/2016 | Spivey et al. | |
| 9,750,521 B2 | 9/2017 | Lamping et al. | |
| 9,949,785 B2 | 4/2018 | Price et al. | |
| 2015/0148829 A1 | 5/2015 | Kimball et al. | |
| 2015/0245850 A1 | 9/2015 | Hibner et al. | |
| 2016/0015419 A1 * | 1/2016 | Hibner | A61B 17/32009 606/171 |
| 2017/0000541 A1 | 1/2017 | Yates et al. | |

* cited by examiner

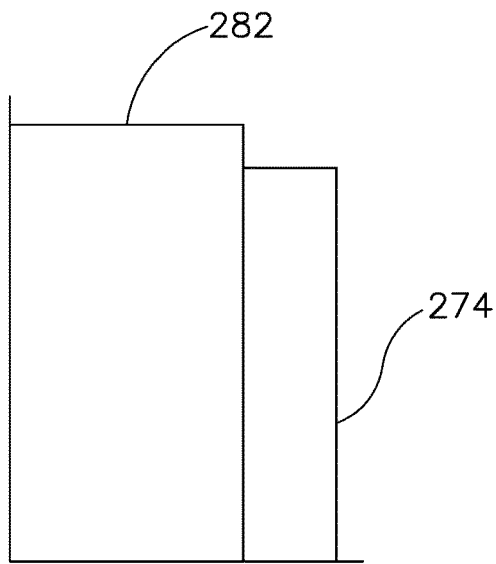
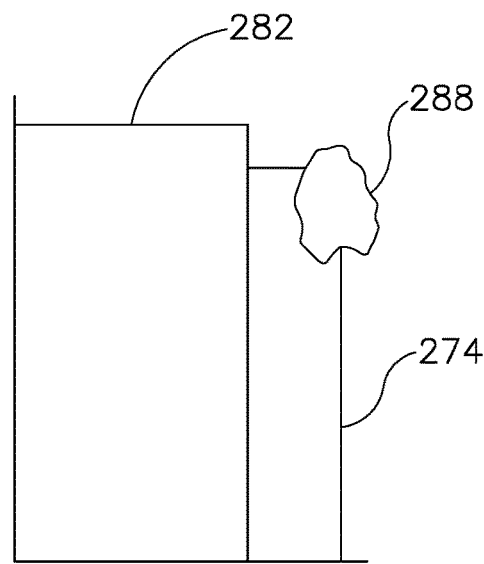
Fig.28A        Fig.28B
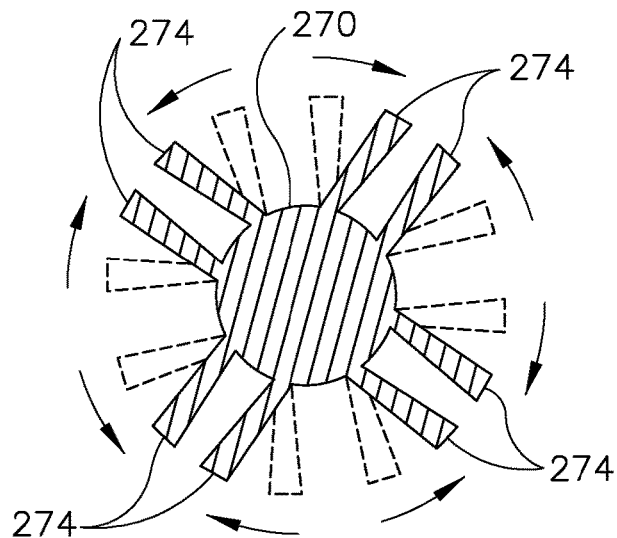
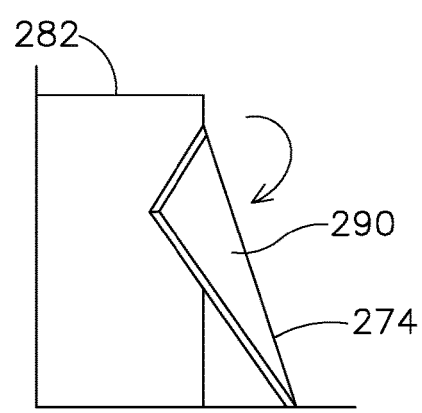
Fig.29A        Fig.29B

ACOUSTIC DRIVETRAIN WITH EXTERNAL COLLAR AT NODAL POSITION

BACKGROUND

Ultrasonic surgical instruments utilize ultrasonic energy for both precise cutting and controlled coagulation of tissue. The ultrasonic energy cuts and coagulates by vibrating a blade in contact with the tissue. Vibrating at frequencies of approximately 50 kilohertz (kHz), for example, the ultrasonic blade denatures protein in the tissue to form a sticky coagulum. Pressure exerted on the tissue with the blade surface collapses blood vessels and allows the coagulum to form a hemostatic seal. The precision of cutting and coagulation may be controlled by the surgeon's technique and adjusting the power level, blade edge, tissue traction, and blade pressure, for example.

Examples of ultrasonic surgical devices include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," issued Nov. 9, 1999, the disclosure of which is incorporated by reference herein; U.S. Pat. No. 6,283,981, entitled "Method of Balancing Asymmetric Ultrasonic Surgical Blades," issued Sep. 4, 2001, the disclosure of which is incorporated by reference herein; U.S. Pat. No. 6,309,400, entitled "Curved Ultrasonic Blade having a Trapezoidal Cross Section," issued Oct. 30, 2001, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,423,082, entitled "Ultrasonic Surgical Blade with Improved Cutting and Coagulation Features," issued Jul. 23, 2002, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 8,057,498, entitled "Ultrasonic Surgical Instrument Blades," issued Nov. 15, 2011, the disclosure of which is incorporated by reference herein; U.S. Pat. No. 8,461,744, entitled "Rotating Transducer Mount for Ultrasonic Surgical Instruments," issued Jun. 11, 2013, the disclosure of which is incorporated by reference herein; U.S. Pat. No. 8,591,536, entitled "Ultrasonic Surgical Instrument Blades," issued Nov. 26, 2013, the disclosure of which is incorporated by reference herein; U.S. Pat. No. 8,623,027, entitled "Ergonomic Surgical Instruments," issued Jan. 7, 2014, the disclosure of which is incorporated by reference herein; U.S. Pat. No. 9,095,367, entitled "Flexible Harmonic Waveguides/Blades for Surgical Instruments," issued Aug. 4, 2015, the disclosure of which is incorporated by reference herein; and U.S. Pub. No. 2016/0022305, entitled "Ultrasonic Blade Overmold," published Jan. 28, 2016, issued as U.S. Pat. No. 9,750,521 on Sep. 5, 2017, the disclosure of which is incorporated by reference herein.

An ultrasonic surgical instrument generally includes a handle assembly that supports an ultrasonic transducer, a shaft assembly coupled to the handle assembly and housing a waveguide acoustically coupled to the ultrasonic transducer, and an end effector coupled to a distal end of the shaft assembly and having an ultrasonic blade acoustically coupled to a distal end of the waveguide. The waveguide is configured to communicate ultrasonic energy from the ultrasonic transducer to the ultrasonic blade for treating tissue positioned in contact with the blade. During use of the ultrasonic surgical instrument it may be desirable to rotate the end effector relative to the handle assembly, by rotating the shaft assembly, to thereby reorient the end effector relative to tissue being treated. Conventional ultrasonic surgical instruments include a rotation member, such as a knob, that is rotationally coupled to the shaft assembly, including the waveguide, and is configured to be gripped by the user to thereby rotate the shaft assembly and the end effector relative to the handle assembly.

While various types of ultrasonic surgical instruments and structures for rotationally coupling the shaft assembly, including the waveguide, to the rotation member have been made and used, it is believed that no one prior to the inventor(s) has made or used the invention described herein.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 28A depicts an enlarged side elevational view of a proximal end of the torque transfer collar and a spline of the waveguide of FIG. 27B;

FIG. 28B depicts a side elevational view of the torque transfer collar and the spline of the FIG. 28A, showing a proximal end of the spline deformed according to a first exemplary configuration;

FIG. 29A depicts a sectional end view of the waveguide of FIG. 27A, showing proximal ends of the splines being deformed according to a second exemplary configuration;

FIG. 29B depicts an enlarged side elevational view of a proximal end of the torque transfer collar and a spline of the waveguide of FIG. 27B, showing the spline deformed according to the second configuration shown in FIG. 29A;

Figure 1:
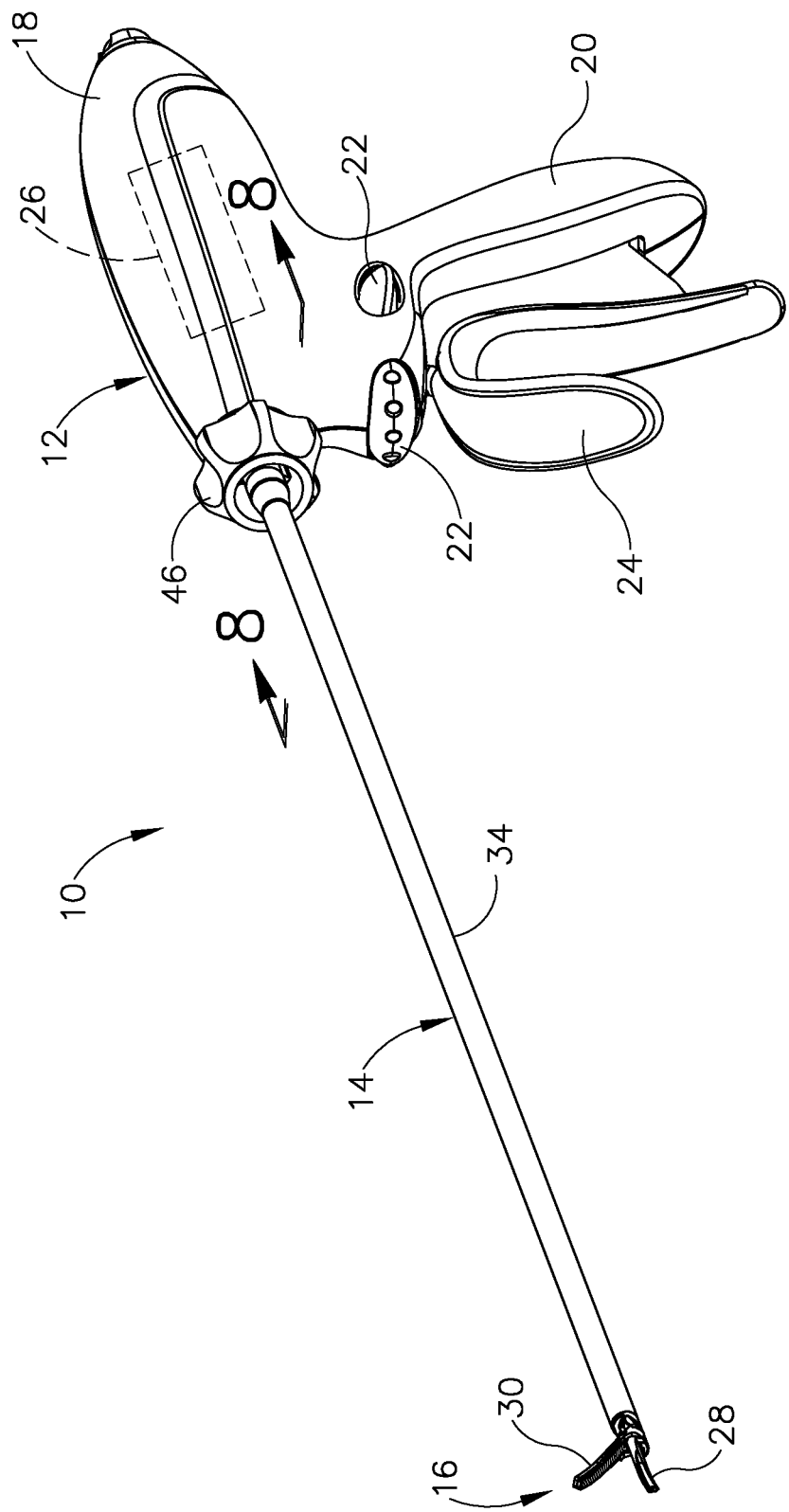
FIG. 1 depicts a perspective view of an exemplary ultrasonic surgical instrument.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

For clarity of disclosure, the terms "proximal" and "distal" are defined herein relative to a surgeon, or other operator, grasping a surgical instrument having a distal surgical end effector. The term "proximal" refers to the position of an element arranged closer to the surgeon, and the term "distal" refers to the position of an element arranged closer to the surgical end effector of the surgical instrument and further away from the surgeon. Moreover, to the extent that spatial terms such as "upper," "lower," "vertical," "horizontal," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

I. EXEMPLARY ULTRASONIC SURGICAL INSTRUMENT HAVING TORQUE TRANSFER STRUCTURE

A. Overview of Exemplary Ultrasonic Surgical Instrument

Figure 2:
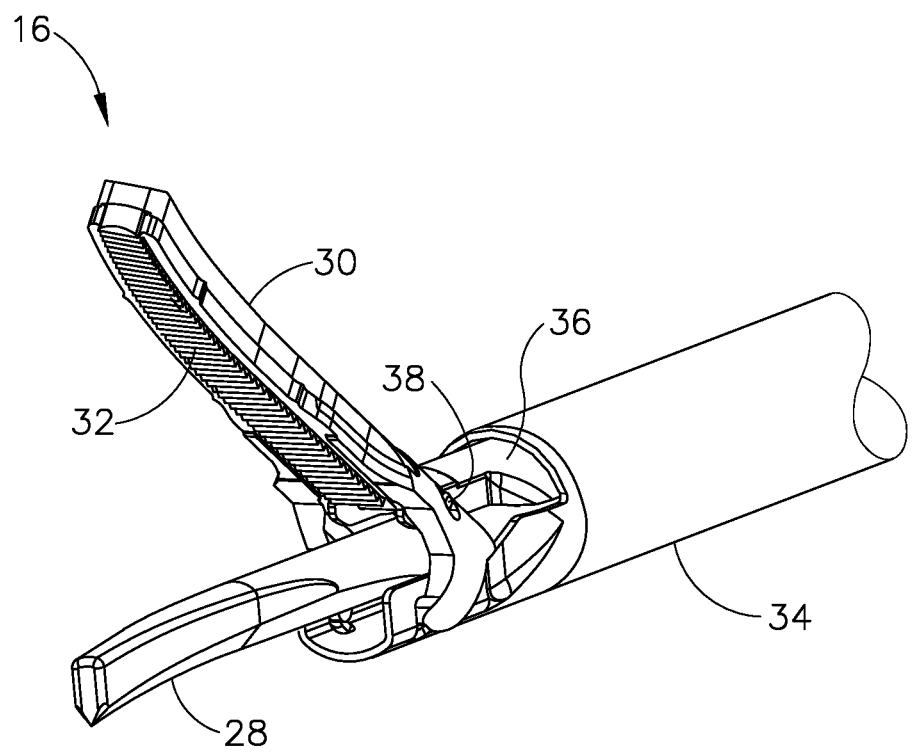
FIG. 2 depicts a perspective view of an end effector of the ultrasonic surgical instrument of FIG. 1.

FIGS. 1 and 2 show an exemplary ultrasonic surgical instrument (10) that includes a handle assembly (12), a shaft assembly (14) extending distally from handle assembly (12), and an end effector (16) arranged at a distal end of shaft assembly (14). Handle assembly (12) comprises a body (18) including a pistol grip (20) and energy control buttons (22) configured to be manipulated by a surgeon to control various aspects of tissue treatment energy delivered by surgical instrument (10). A trigger (24) is coupled to a lower portion of body (18) and is pivotable toward and away from pistol grip (20) to selectively actuate end effector (16). In other suitable variations of surgical instrument (10), handle assembly (12) may comprise a scissor grip configuration, for example. Body (18) houses an ultrasonic transducer (26), shown schematically in FIG. 1, configured to deliver ultrasonic energy to end effector (16).

As shown best in FIG. 2, end effector (16) includes an ultrasonic blade (28) and a clamp arm (30) configured to selectively pivot toward and away from ultrasonic blade (28), for clamping tissue therebetween. Clamp arm (30) includes a clamp pad (32) arranged on a clamping side thereof. Ultrasonic blade (28) is acoustically coupled with ultrasonic transducer (26), which is configured to drive (i.e., vibrate) ultrasonic blade (28) at ultrasonic frequencies for cutting and/or sealing tissue positioned in contact with ultrasonic blade (28). Clamp arm (30) is operatively coupled with trigger (24) such that clamp arm (30) is configured to pivot toward ultrasonic blade (28), to a closed position (not shown), in response to pivoting of trigger (24) toward pistol grip (20). Further, clamp arm (30) is configured to pivot away from ultrasonic blade (28) to an open position, shown in FIGS. 1 and 2, in response to pivoting of trigger (24) away from pistol grip (20). Various suitable ways in which clamp arm (30) may be coupled with trigger (24) will be apparent to those of ordinary skill in the art in view of the teachings provided herein. In some versions, one or more resilient members may be incorporated to bias clamp arm (30) and/or trigger (24) toward the open position.

Figure 3:
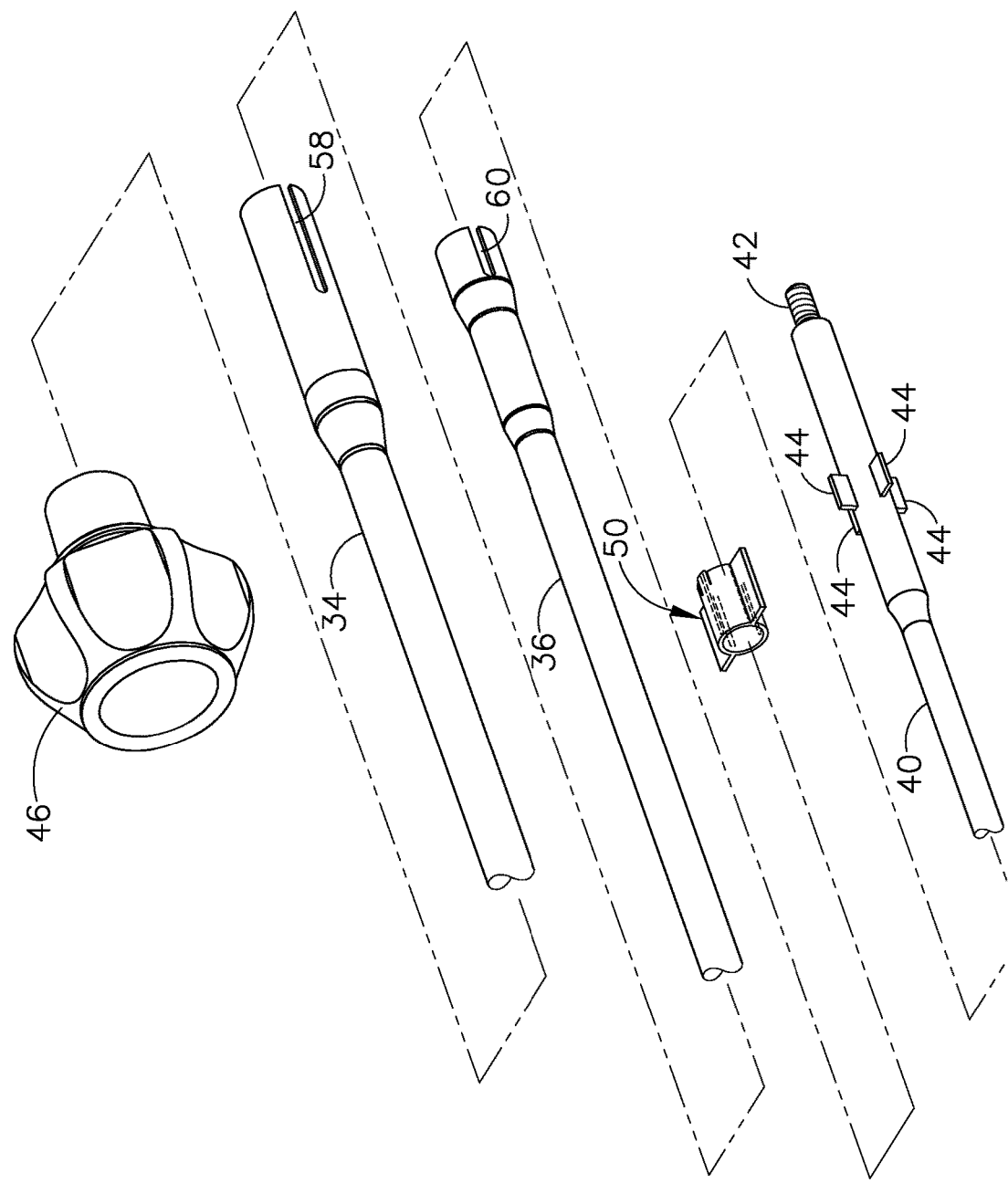
FIG. 3 depicts a disassembled view of a shaft assembly, a rotation knob, and a torque transfer collar of the ultrasonic surgical instrument of FIG. 1.

As shown in FIGS. 1 and 3, shaft assembly (14) extends along a longitudinal shaft axis and includes an outer tube (34) and an inner tube (36) received within outer tube (34). As shown in FIG. 2, a proximal end of clamp arm (30) is pivotally coupled to distal ends of outer and inner tubes (34, 36), thereby enabling clamp arm (30) to pivot relative to shaft assembly (14) about a pivot axis defined by a pivot pin (38) extending transversely through the distal end of inner tube (36). In the present example, inner tube (36) is longitudinally fixed relative to handle assembly (18), and outer tube (34) is configured to translate relative to inner tube (36) and handle assembly (18), along the longitudinal axis of shaft assembly (20). As outer tube (34) translates distally, clamp arm (30) pivots about its pivot axis toward its open position. As outer tube (34) translates proximally, clamp arm (30) pivots about its pivot axis in an opposite direction toward its closed position. Though not shown, a proximal end of outer tube (34) is operatively coupled with trigger (24) such that actuation of trigger (24) causes translation of outer tube (34) relative to inner tube (36), thereby opening or closing clamp arm (30). In other suitable configurations not shown herein, outer tube (34) may be longitudinally fixed and inner tube (36) may be configured to translate for moving clamp arm (30) between its open and closed positions. Various other suitable mechanisms for actuating clamp arm (30) between its open and closed positions will be apparent to those of ordinary skill in the art.

Shaft assembly (14) further includes an ultrasonic waveguide (40) supported within and extending longitudinally through inner tube (36). Ultrasonic blade (28) is formed integrally with and extends distally from a distal end of waveguide (40). A threaded proximal end (42) of waveguide (40) is configured to threadedly couple with a threaded distal end (not shown) of ultrasonic transducer (26). In exemplary configurations, ultrasonic transducer (26) and waveguide (40) may be threadedly coupled together using any of the exemplary torque wrench features disclosed in U.S. Pat. App. No. 15/644,944, entitled "Features to Couple Acoustic Drivetrain Components in Ultrasonic Surgical Instrument," filed on Jul. 10, 2017, issued as U.S. Pat. No. 10,709,470 on Jul. 14, 2020, the disclosure of which is incorporated by reference herein. Waveguide (40) acoustically couples ultrasonic transducer (26) with ultrasonic blade (28), and is configured to communicate ultrasonic mechanical vibrations from transducer (26) to blade (28) during use. In this manner, ultrasonic transducer (26), waveguide (40), and ultrasonic blade (28) together define an acoustic assembly of ultrasonic surgical instrument (10).

A radially enlarged proximal portion of waveguide (40) includes a nodal coupling feature in the form of splines (44) that project radially outwardly from an outer surface of waveguide (40), and are arranged circumferentially about waveguide (40) at an acoustic node thereof. As described in greater detail below, splines (44) are configured to couple waveguide (40) rotationally and axially with a torque transfer structure (50), which in turn couples with a rotation knob (46). While waveguide (40) of the present example is shown having four splines (44) arranged uniformly about the outer circumference of waveguide (40), it will be appreciated that splines (44) may be provided in various other quantities and circumferential arrangements in other examples.

Ultrasonic transducer (26) is electrically coupled with a generator (not shown), which may be provided externally of or integrated within ultrasonic surgical instrument (10). During use, the generator powers ultrasonic transducer (26) to produce ultrasonic mechanical vibrations, which are communicated distally through waveguide (40) to ultrasonic blade (28). Ultrasonic blade (28) is caused to oscillate longitudinally in the range of approximately 10 to 500 microns peak-to-peak, for example, and in some instances in the range of approximately 20 to 200 microns, at a predetermined vibratory frequency $f_0$ of approximately 50 kHz, for example. Vibrating ultrasonic blade (28) may be positioned in direct contact with tissue, with or without assistive clamping force provided by clamp arm (30), to impart ultrasonic vibrational energy to the tissue and thereby cut and/or seal the tissue. For example, blade (28) may cut through tissue clamped between clamp arm (30) and a clamping side of blade (28), or blade (28) may cut through tissue positioned in contact with an oppositely disposed non-clamping side of blade (28) having an edge, for example during a "back-cutting" movement. In some versions, waveguide (40) may be configured to amplify the ultrasonic vibrations delivered to blade (28). Waveguide (40) may include various features operable to control the gain of the vibrations, and/or features suitable to tune waveguide (40) to a selected resonant frequency.

B. Exemplary Torque Transfer Collar Having Snap Arms

Shaft assembly (14) and end effector (16) are configured to rotate together relative to body (18) about the longitudinal shaft axis. As shown in FIGS. 1 and 3, ultrasonic surgical instrument (10) further includes a rotation knob (46) secured to a proximal end of shaft assembly (14) and rotatably coupled to a distal end of body (18) of handle assembly (12). Rotation knob (46) encircles and is rotationally fixed to shaft assembly (14), including waveguide (40), by a torque transfer structure (50) (also referred to as a "torque adapter" or a "grounding adapter") arranged at a proximal acoustic node of waveguide (40). Accordingly, rotation knob (46) may be gripped by a user to selectively manipulate the rotational orientation of shaft assembly (14) and end effector (16) relative to handle assembly (12). Though not shown, rotation knob (46) may be comprised of first and second circumferential halves that couple together, for example by snap-fit or press-fit engagement, about shaft assembly (14).

Torque transfer structure (50) of the present example is shown in the form of a torque transfer collar (also referred to as a "grounding collar" or a "grounding ring") that encircles waveguide (40) at a proximal acoustic node of waveguide (40). As described in greater detail below, torque transfer collar (50) includes inner features that secure collar (50) rotationally and axially relative to waveguide (40), as well as outer features that secure collar (50) rotationally with inner tube (36), outer tube (34), and rotation knob (46). Accordingly, torque transfer collar (50) is configured to transfer an input torque exerted on rotation knob (46), to the components of shaft assembly (14), including waveguide (40), to thereby rotate shaft assembly (14) and end effector (16) about the longitudinal shaft axis relative to handle assembly (12).

Figure 4:
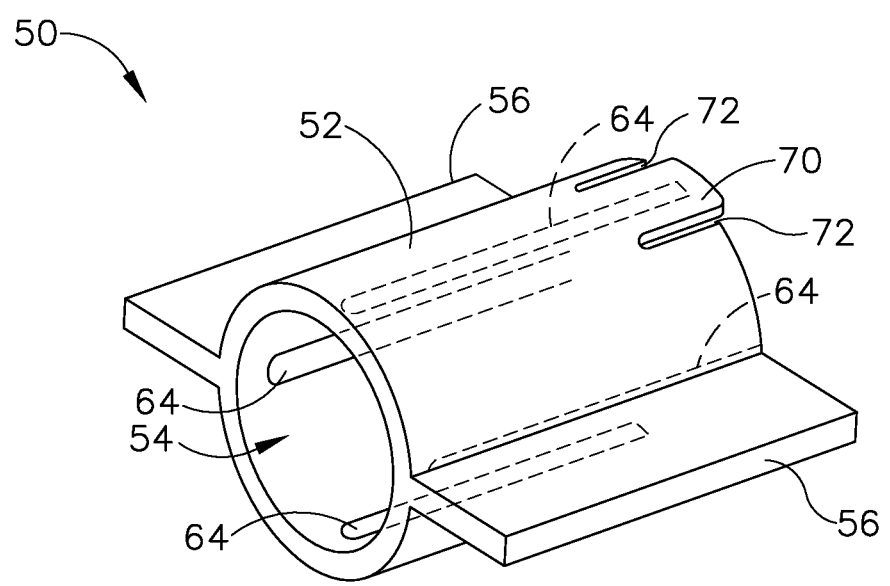
FIG. 4 depicts a perspective view of the torque transfer collar of FIG. 3.
Figure 5:
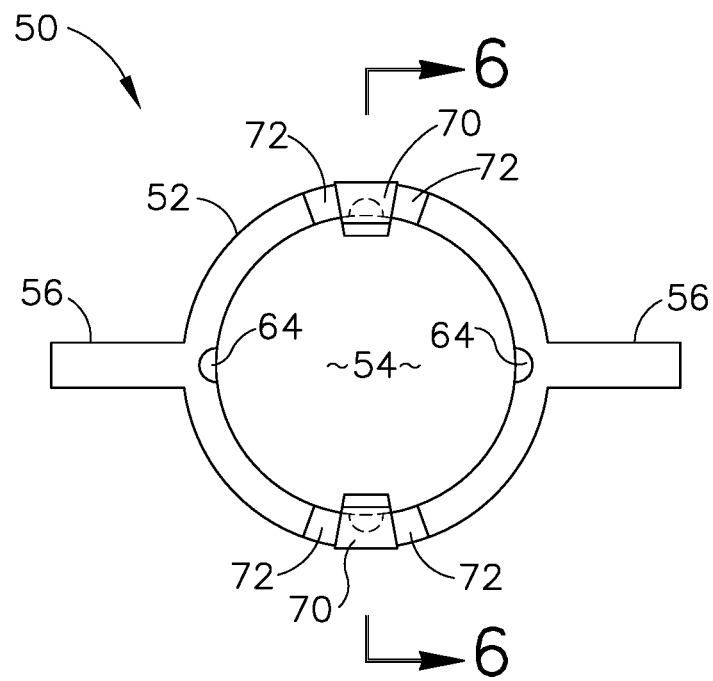
FIG. 5 depicts a rear elevational view of the torque transfer collar of FIG. 4.
Figure 8:
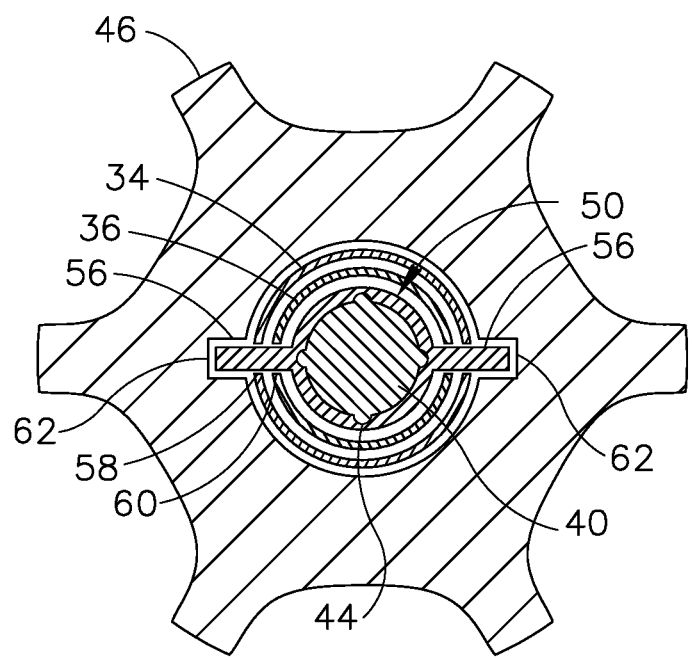
FIG. 8 depicts an end sectional view taken along section line 8-8 in FIG. 1, showing rotational coupling of the torque transfer collar, the shaft assembly, and the rotation knob.

As shown best in FIG. 4, torque transfer collar (50) includes a cylindrical, annular collar body (52) having an axially extending central passage (54). Central passage (54) is configured to receive waveguide (40) therethrough when collar (50) is applied to waveguide (40) in a proximal direction from a distal end of waveguide (40), for example over ultrasonic blade (28). A pair of tab-like lugs (56) (or "wings") project radially outwardly from collar body (52) at diametrically opposed positions, and define first and second transverse ends of torque transfer collar (50). Lugs (56) are configured to rotationally couple collar (50) with outer tube (34), inner tube (36), and rotation knob (46). As shown in FIGS. 3 and 8, a proximal end of outer tube (34) includes a pair of diametrically opposed outer slots (58) configured to align with and receive lugs (56) therethrough, and a proximal end of inner tube (36) includes a corresponding pair of inner slots (60) configured to align with outer slots (58) and receive lugs (56) therethrough. Outer slots (58) may be sized with an axial length suitable to enable outer tube (34) to translate relative to inner tube (36) to actuate clamp arm (30) between open and closed positions, as described above. As shown in FIG. 8, an interior of rotation knob (46) includes a pair of knob slots (62) configured to receive lugs (56) in a press-fit engagement to thereby fix torque transfer collar (50) rotationally and axially relative to rotation knob (46).

Figure 6:
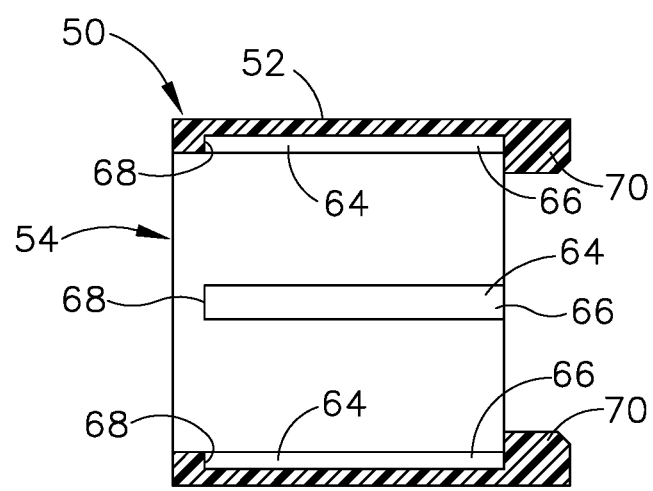
FIG. 6 depicts a side sectional view of the torque transfer collar of FIG. 5, taken along section line 6-6.
Figure 7:
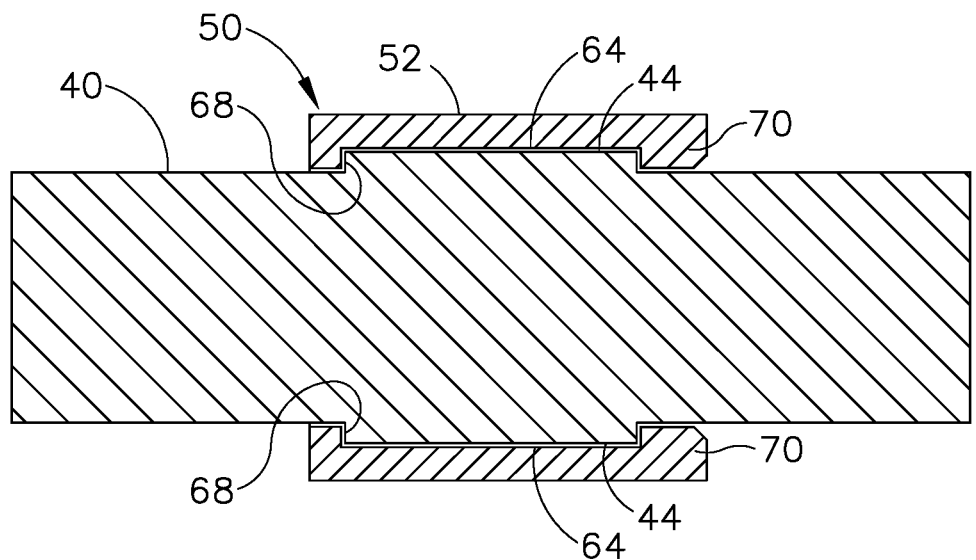
FIG. 7 depicts a side sectional view of the torque transfer collar and a waveguide of FIG. 3.

As shown in FIGS. 4-7, an interior of torque transfer collar (50) includes a torque coupling feature (or "keying feature") in the form of a plurality of axially extending slots (64) configured as grooves arranged circumferentially about an inner surface of collar body (52). As shown best in FIG. 6, each axial slot (64) includes an open proximal end (66) that opens to a proximal end of collar body (52), and a closed distal end (68) spaced proximally from a distal end of collar body (52). As shown in FIG. 7, each axial slot (64) is configured to receive a respective spline (44) of waveguide (40) therein, thereby securing torque transfer collar (50) rotationally relative to waveguide (40). Additionally, one or more waveguide splines (44) may be keyed to one or more collar slots (64) such that torque transfer collar (50) must be oriented in one or more predetermined rotational orientations relative to waveguide (40) in order for collar (50) to properly couple with waveguide (40). In the present example, torque transfer collar (50) includes four axial slots (64) configured to align with the four splines (44) of waveguide (40), though it will be appreciated that axial slots (64) may be provided in various alternative quantities and circumferential arrangements to accommodate alternative quantities and circumferential arrangements of splines (44).

As also shown throughout FIGS. 4-7, torque transfer collar (50) further includes a pair of snap members in the form of snap arms (70) configured to couple to waveguide splines (44) with a snap-fit engagement. Snap arms (70) project proximally from a proximal end of collar body (52), and radially inwardly toward a central axis of collar body (52). In the present example, snap arms (70) are arranged at diametrically opposed positions such that snap arms (70) are positioned to engage a diametrically opposed pair of splines (44). In other examples, however, snap arms (70) may be provided in various other arrangements and quantities. As shown best in FIGS. 4 and 5, each snap arm (70) is positioned between a pair of relief notches (72) that enable snap arm (70) to resiliently flex radially outwardly relative to collar body (52) when engaging a corresponding waveguide spline (44) as torque transfer collar (50) is slid proximally along waveguide (40) and over splines (44). As shown in FIGS. 6 and 7, each snap arm (70) terminates at a chamfered proximal end that facilitates radially outward flexing of snap arm (70) over its respective spline (44) as torque transfer collar (50) is coupled to waveguide (40).

As shown in FIG. 7, torque transfer collar (50) is constrained axially relative to waveguide (40) once coupled together. In particular, closed distal end (68) of each axial slot (64) of collar (50) provides a proximally facing surface configured to abut a distally facing surface of the respective spline (44) of waveguide (40), thereby limiting proximal axial movement of torque transfer collar (50) relative to waveguide (40). Additionally, a distally facing surface of each snap arm (70) is configured to abut a proximally facing surface of the respective spline (44), thereby limiting distal axial movement of torque transfer collar (50) relative to waveguide (40).

FIG. 8 shows additional details of the coaxial rotational coupling between waveguide (40), outer and inner tubes (34, 36), and rotation knob (46). In particular, waveguide (40) is rotationally coupled with torque transfer collar (50) via waveguide splines (44), and torque transfer collar (50) is rotationally coupled with inner tube (36), outer tube (34), and rotation knob (46) via collar lugs (56). Accordingly, as described above, an input torque exerted on rotation knob (46) by a user is ultimately transmitted to waveguide (40) via collar lugs (56) and waveguide splines (44), thereby causing outer and inner tubes (34, 36), waveguide (40), and ultrasonic blade (28) to rotate together with rotation knob (46) about the shaft axis. In various examples, torque transfer collar (50) may be formed of any suitably resilient polymeric material, such as a plastic, thereby mitigating risk of damage to waveguide (40) during use otherwise created by contacting waveguide (40) with a torque transfer structure formed of a hard material, such as a metal. Furthermore, torque transfer collar (50) provides an effective rotational coupling between waveguide (40), tubes (34, 36), and rotation knob (46) without directing a coupling structure, such as a pin, transversely through the central axis of waveguide (40), thereby maintaining optimal structural integrity of waveguide (40) during use. It will be understood that the additional exemplary torque transfer collars described below may be formed of similar materials and be configured to provide similar functional benefits.

C. Exemplary Torque Transfer Collar Having Crush Ribs

Figure 9A:
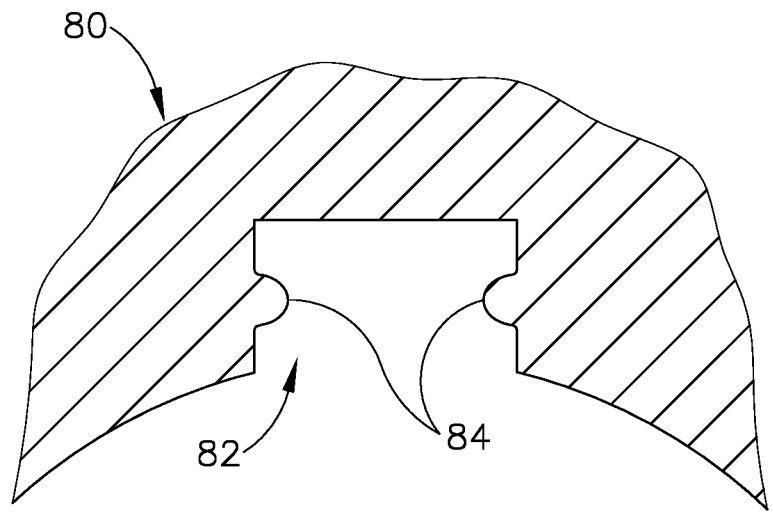
FIG. 9A depicts an enlarged end sectional view of another exemplary torque transfer collar.
Figure 9B:
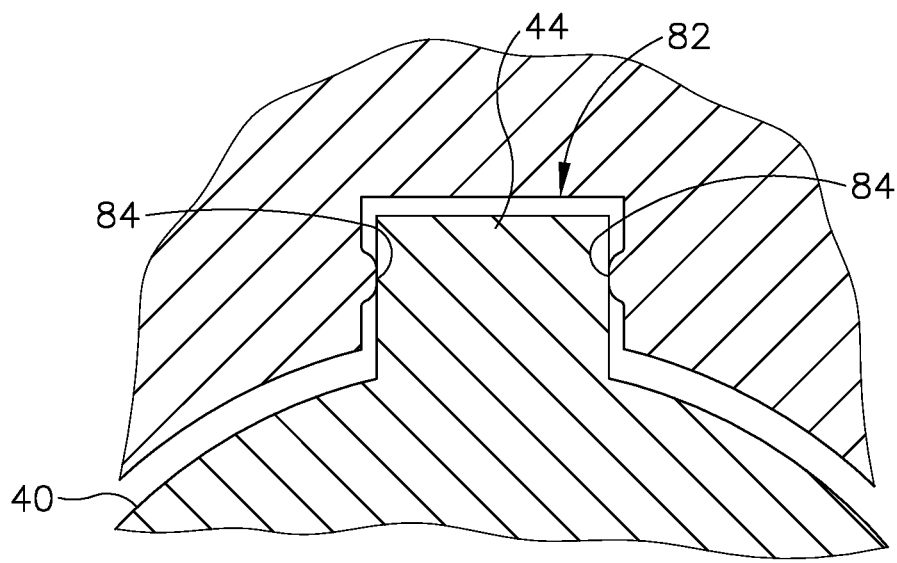
FIG. 9B depicts an enlarged end sectional view of the torque transfer collar of FIG. 9A in combination with the waveguide of FIG. 3.

FIGS. 9A and 9B show another exemplary torque transfer collar (80) suitable for use in ultrasonic surgical instrument (10). Collar (80) is generally similar to collar (50) described above as indicated by use of like reference numerals in FIGS. 9A and 9B. Collar (80) differs from collar (50) in that collar (80) includes axial slots (82) having crush ribs (84) configured to plastically deform against waveguide splines (44) as collar (80) is coupled with waveguide (40), as shown in FIG. 9B. In the present example, crush ribs (84) are arranged on opposed sides of each axial slot (82) and extend axially through axial slot (82). In some examples, crush ribs (84) may taper proximally so as to define a lead-in feature at the open proximal end of axial slot (82) that facilitates proximal advancement of torque transfer collar (80) over waveguide splines (44). Advantageously, the deformation of crush ribs (84) against waveguide splines (44) provides an enhanced press-fit coupling between waveguide (40) and torque transfer collar (80), thereby minimizing the risk of unintended decoupling of waveguide (40) from collar (80), for example when ultrasonic surgical instrument (10) is dropped from an elevated position.

Figure 10:
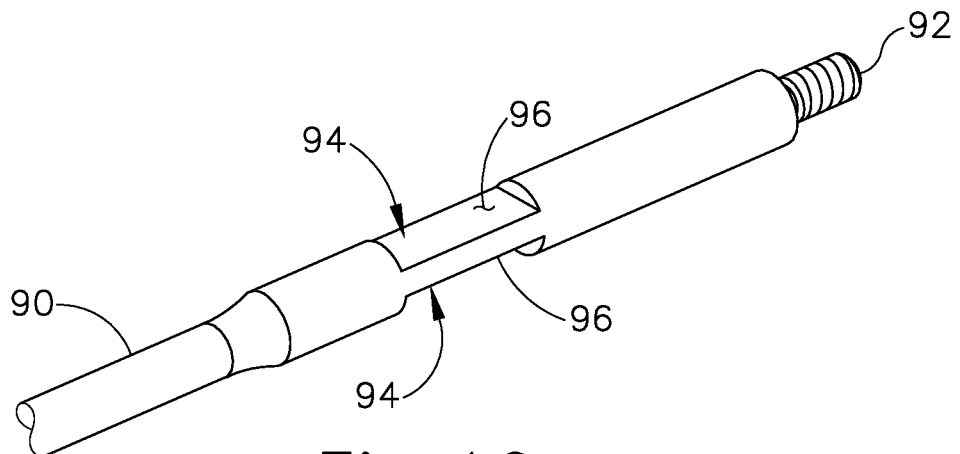
FIG. 10 depicts a perspective view of a proximal portion of another exemplary waveguide.
Figure 11:
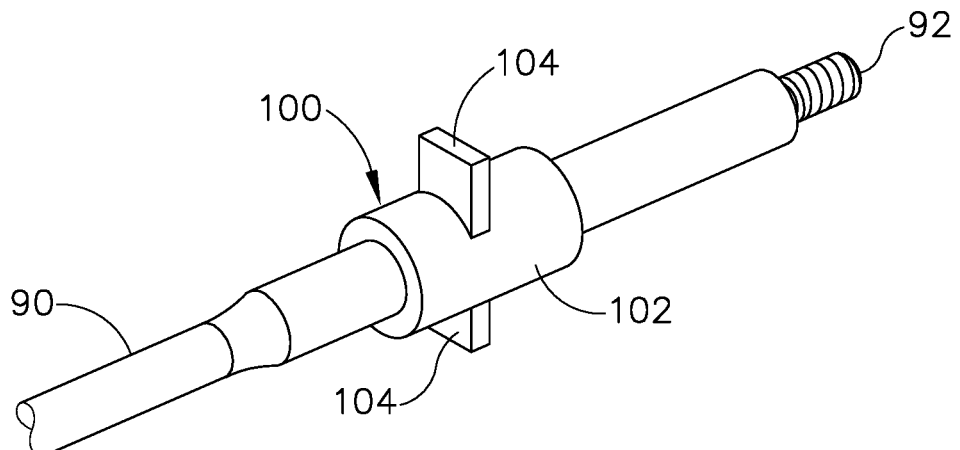
FIG. 11 depicts a perspective view of the proximal portion of the waveguide of FIG. 10, in combination with another exemplary torque transfer collar.
Figure 12:
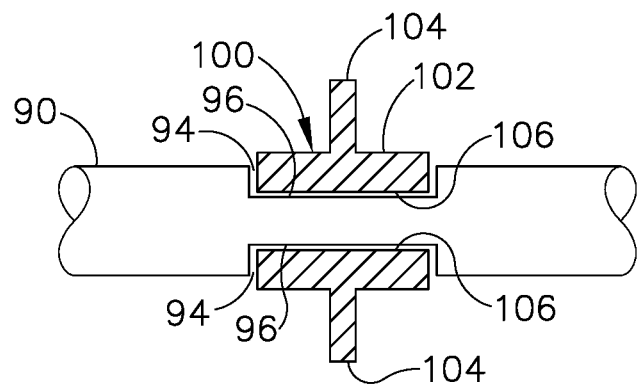
FIG. 12 depicts a side sectional view of the waveguide and torque transfer collar of FIG. 11.

D. Exemplary Waveguide Having Slots with Planar Base Surfaces and Torque Transfer Collar Received within Slots FIGS. 10-12 show another exemplary waveguide (90) and a corresponding torque transfer collar (100) suitable for use in ultrasonic surgical instrument (10). Waveguide (90) is similar to waveguide (40) in that waveguide (90) includes a threaded proximal end (92) configured to threadedly couple with a distal end of ultrasonic transducer (26), and waveguide (90) is configured to communicate ultrasonic energy from transducer (26) to ultrasonic blade (28). Waveguide (90) includes a nodal coupling feature in the form of a pair of slots (94) recessed inwardly of an outer surface of waveguide (90) at a proximal acoustic node of waveguide (90). Slots (94) are diametrically opposed from one another, and each slot (94) is configured as a "flat" that extends axially between closed proximal and distal ends to define a planar base surface (96).

As shown in FIG. 11, torque transfer collar (100) includes a cylindrical collar body (102) that encircles waveguide (90), and a pair of tab-like lugs (104) extending radially outwardly from collar body (102) at diametrically opposed positions. In the present example, each lug (104) is oriented such that a length thereof extends transversely to a longitudinal axis of collar body (102) and waveguide (90). Similar to lugs (56) of collar (50), lugs (104) are configured to rotationally couple collar (100) with outer and inner tubes (34, 36) and rotation knob (46), as well as secure collar (100) axially relative to rotation knob (46). In that regard, it will be appreciated that outer slots (58), inner slots (60), and knob slots (62) may be suitably modified to accommodate the transverse orientation of lugs (104).

As shown in FIG. 12, torque transfer collar (100) is fixed rotationally and axially relative to waveguide (90). In particular, an interior of collar body (102) includes a pair of inwardly projecting portions (106) that are received within respective slots (94) of waveguide (90) and engage planar base surfaces (96), thereby securing collar (100) rotationally relative to waveguide (90). Additionally, distally facing collar surfaces defined by a distal end of collar (100) are configured to abut respective proximally facing surfaces defined by distal ends of slots (94). Similarly, proximally facing collar surfaces defined by a proximal end of collar (100) are configured to abut respective distally facing surfaces defined by proximal ends of slots (94). In this manner, collar (100) is secured axially relative to waveguide (90). In various examples, torque transfer collar (100) may be overmolded over waveguide (90) such that an inner surface of collar (100) conforms to slots (94) and a rounded outer surface of waveguide (90). Collar (100) presents functional benefits similar to those described above in connection with collar (50).

Figure 13:
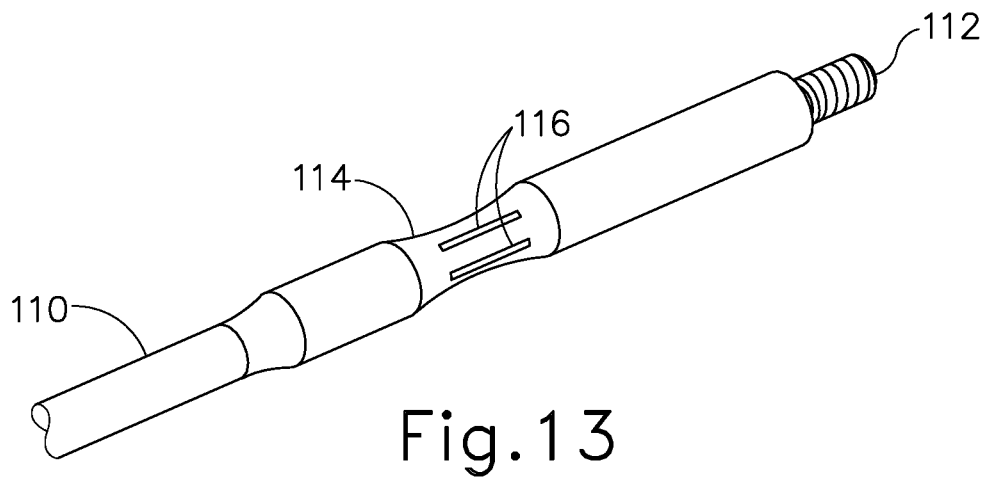
FIG. 13 depicts a perspective view of a proximal portion of another exemplary waveguide.

E. Exemplary Waveguide and Torque Transfer Collars Having First and Second Mating Components FIG. 13 shows another exemplary waveguide (110) suitable for use in ultrasonic surgical instrument (10). Waveguide (110) is similar to waveguide (40) in that waveguide (110) includes a threaded proximal end (112) configured to threadedly couple with a distal end of ultrasonic transducer (26), and waveguide (110) is configured to communicate ultrasonic energy from transducer (26) to ultrasonic blade (28). Waveguide (110) includes a narrowed proximal portion (114) formed at a proximal acoustic node of waveguide (110), and a nodal coupling feature in the form of slots (116) formed in narrowed proximal portion (114). Slots (116) extend axially along and are arranged circumferentially about waveguide (110). In the present example, waveguide (110) includes four slots (116) arranged with uniform circumferential spacing, though it will be understood that various other quantities and circumferential arrangements of slots (116) may be provided.

Figure 14:
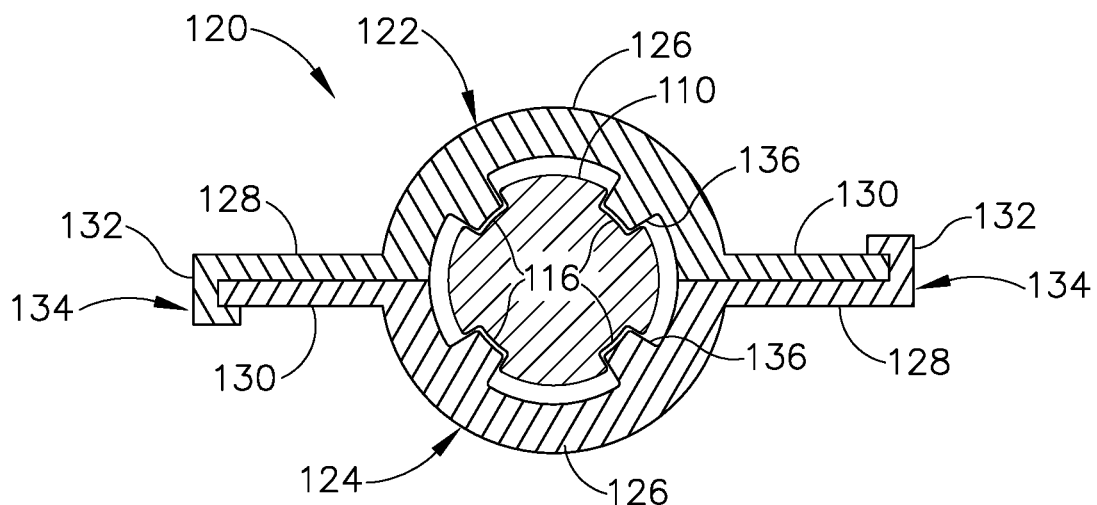
FIG. 14 depicts an end sectional view of the waveguide of FIG. 13 in combination with another exemplary torque transfer collar having first and second coupled components.

FIG. 14 shows a first exemplary torque transfer collar (120) configured for use with waveguide (110). Torque transfer collar (120) includes a first collar half (122) and an opposed second collar half (124) configured to mate together to encircle and engage waveguide (110) at its nodal coupling feature. Each collar half (122, 124) includes a semi-cylindrical body portion (126), a first lug arm (128) extending radially outwardly from a first transverse end of body portion (126), and an opposed second lug arm (130) extending radially outwardly from an opposed second transverse end of body portion (126). A terminal end of first lug arm (128) of each collar half (122, 124) includes a clip portion (132) configured to receive and retain the terminal end of second lug arm (130) of the opposing collar half (122, 124), for example in a snap-fit engagement, thereby coupling collar halves (122, 124) together. Each coupled pair of first and second lug arms (128, 130) defines a respective lug (134) of torque transfer collar (120). Lugs (134) are configured to secure collar (120) rotationally and axially relative to rotation knob (46), similar to lugs (56) described above.

An interior of each collar half (122, 124) of torque transfer collar (120) includes a pair of inner projections (136) extending radially inwardly toward waveguide (110). As shown, each inner projection (136) is configured to be received within a respective slot (116) formed in waveguide (110) to thereby secure torque transfer collar (120) rotationally and axially relative to waveguide (110). In that regard, a proximal end of each inner projection (136) is configured to abut a closed proximal end of the respective waveguide slot (116), and a distal end of each inner projection (136) is configured to abut a closed distal end of the respective waveguide slot (116), thereby securing collar (120) axially relative to waveguide (110).

Figure 15:
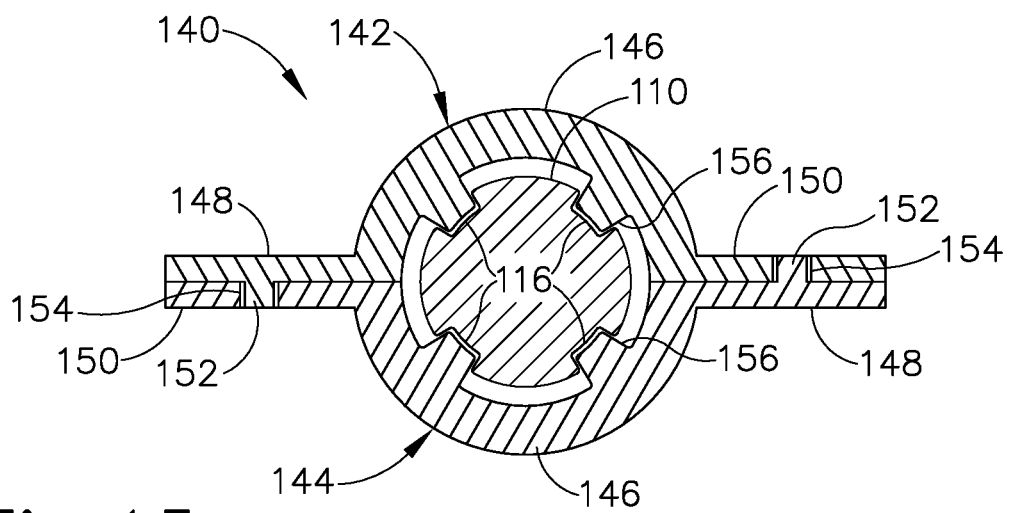
FIG. 15 depicts an end sectional view of the waveguide of FIG. 13 in combination with another exemplary torque transfer collar having first and second coupled components.

FIG. 15 shows a second exemplary torque transfer collar (140) configured for use with waveguide (110). Collar (140) is similar to collar (120) in that collar (140) includes a first collar half (142) and an opposed second collar half (144) configured to mate together to encircle and engage waveguide (110) at its nodal coupling feature. Each collar half (142, 144) includes a semi-cylindrical body portion (146) and is generally similar to collar halves (122, 124) described above, except as otherwise described below. In particular, a first lug arm (148) of each collar half (142, 144) includes a coupling projection (152) extending toward second lug arm (150) of the opposing collar half (142, 144). Additionally, second lug arm (150) of each collar half (142, 144) includes a coupling opening (154) sized and shaped to receive and retain coupling projection (150) of the opposed collar half (142, 144), for example with a snap-fit or a press-fit engagement, to thereby couple first and second collar halves (142, 144) together about waveguide (110). An interior of each collar half (142, 144) includes a pair of inner projections (156) configured to engage slots (116) of waveguide (110) in a manner similar to inner projections (136) of collar (120), to thereby secure collar (140) rotationally and axially relative to waveguide (110). Advantageously, the modular configuration of torque transfer collars (120, 140) facilitates efficient installation of torque transfer collars (120, 140) to waveguide (110) during instrument assembly.

F. Exemplary Waveguide and Fiber-Reinforced Torque Transfer Collar

Figure 16:
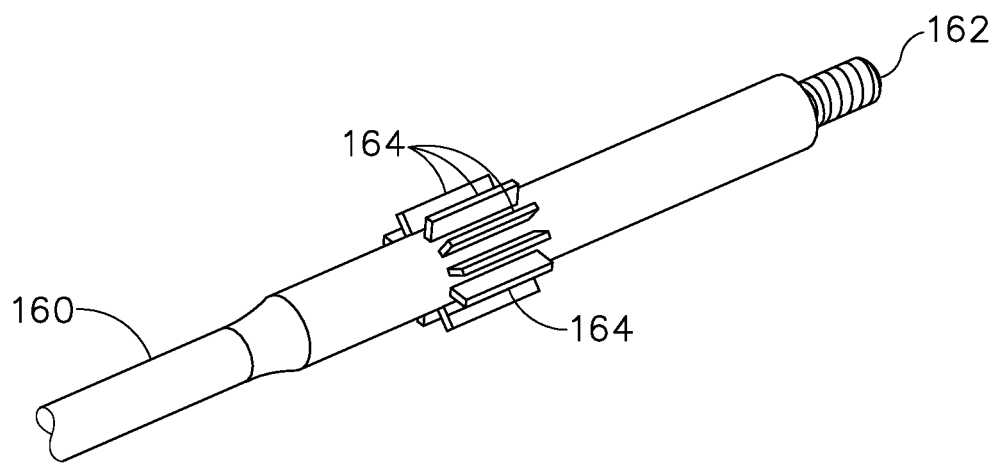
FIG. 16 depicts a perspective view of a proximal portion of another exemplary waveguide.
Figure 17A:
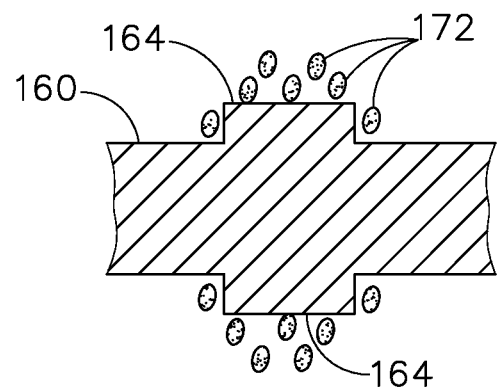
FIG. 17A depicts a side sectional view of the waveguide of FIG. 16 in combination with a plurality of fibers wound circumferentially around the waveguide.
Figure 17B:
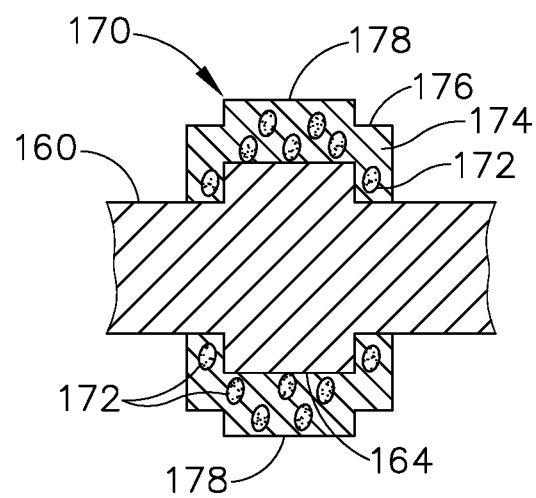
FIG. 17B depicts a side sectional view of the waveguide and fibers of FIG. 17A, after a matrix has been applied to the fibers to form a fiber-reinforced composite torque transfer collar about the waveguide.

FIGS. 16-17B show another exemplary waveguide (160) and a corresponding torque transfer collar (170) suitable for use in ultrasonic surgical instrument (10). Waveguide (160) is similar to waveguide (40) described above in that waveguide (160) includes a threaded proximal end (162) configured to threadedly couple with a distal end of ultrasonic transducer (26), and waveguide (160) is configured to communicate ultrasonic energy from transducer (26) to ultrasonic blade (28). A radially enlarged proximal portion of waveguide (160) includes a nodal coupling feature in the form of splines (164) that project radially outwardly from an outer surface of waveguide (160), and are arranged circumferentially about waveguide (160) at an acoustic node thereof. Splines (164) may be provided in any suitable quantity and circumferential arrangement.

Torque transfer collar (170) of the present example is in the form of a fiber-reinforced composite structure formed circumferentially about splines (164) of waveguide (160). As shown in FIG. 17A, a plurality of fibers (172) are oriented about splines (164) circumferentially, radially, axially, and/or various combinations thereof. Fibers (172) may be formed of any suitable material such as glass, carbon, or Kevlar, for example. The combined waveguide (160) and fibers (172) is then loaded into a molding device (not shown) that is configured to receive a matrix (174) in the region surrounding splines (164) and fibers (172). Matrix (174) conforms to waveguide (160) and cures with the fibers (172) to form fiber-reinforced torque transfer collar (170) about splines (164), as shown in FIG. 17B.

Formed collar (170) includes a collar body (176) comprised of fibers (172) and matrix (174) that engage splines (164) so as to fix collar (170) rotationally and axially relative to waveguide (160). In particular, an interior of cured collar body (176) defines a plurality of alternating axial slots and radially inwardly extending projections that engage splines (164) to thereby fix collar (170) rotationally relative to waveguide (160). Additionally, as shown in FIG. 17B, proximal and distal ends of each spline (164) abut, and may be bonded to, adjacent distally facing and proximally facing inner surfaces of collar (170), thereby fixing collar (170) axially relative to waveguide (160). As also shown in FIG. 17B, formed collar (170) includes a pair of tab-like lugs (178) extending radially outwardly from collar body (176) at diametrically opposed positions. Similar to lugs (56) of torque transfer collar (50), lugs (178) are configured to secure collar (170) rotationally and axially relative to rotation knob (46), as well as couple collar (170) rotationally to outer and inner tubes (34, 36).

Figure 18:
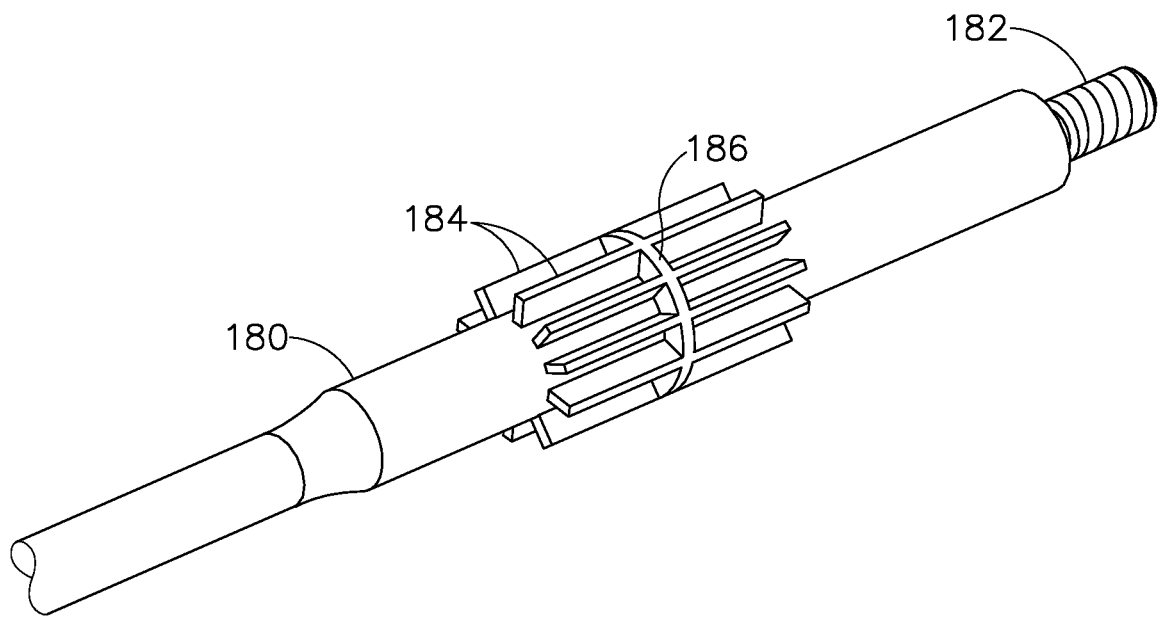
FIG. 18 depicts a perspective view of a proximal portion of another exemplary waveguide.
Figure 19:
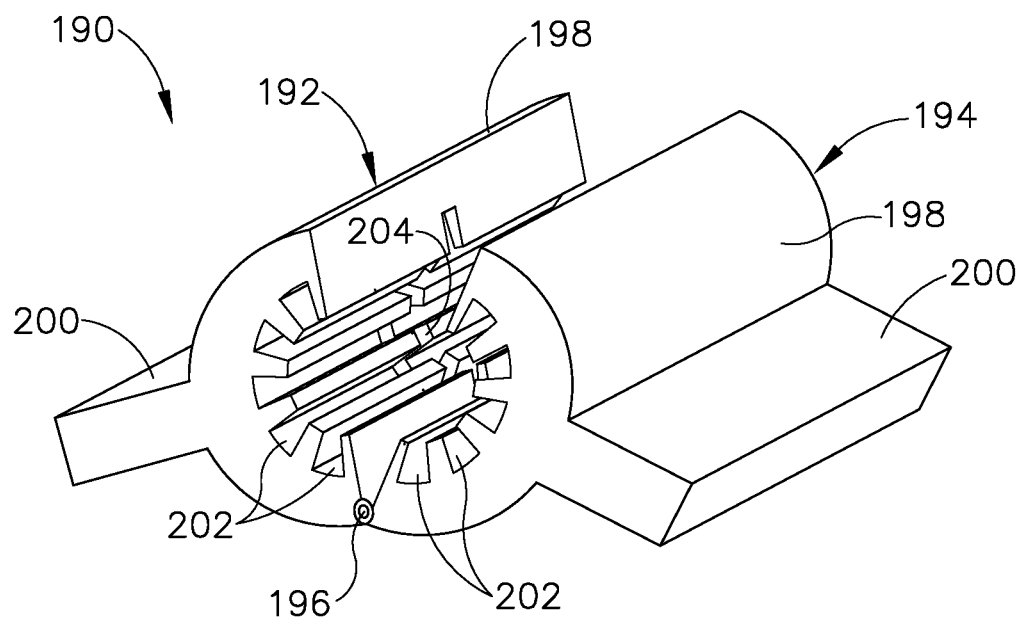
FIG. 19 depicts a perspective view of a torque transfer collar configured for use with the waveguide of FIG. 18, showing first and second coupled components of the torque transfer collar.

G. Exemplary Waveguide Having Circumferential Projection and Torque Transfer Collar Having Circumferential Slot FIGS. 18 and 19 show another exemplary waveguide (180) and a corresponding torque transfer collar (190) suitable for use in ultrasonic surgical instrument (10). As shown in FIG. 18, waveguide (180) is similar to waveguide (40) described above in that waveguide (180) includes a threaded proximal end (182) configured to threadedly couple with a distal end of ultrasonic transducer (26), and waveguide (180) is configured to communicate ultrasonic energy from transducer (26) to ultrasonic blade (28). A radially enlarged proximal portion of waveguide (180) includes a nodal coupling feature in the form of a plurality of splines (184) in combination with a circumferential projection (186) extending radially outwardly from an outer surface of waveguide (180) at an acoustic node thereof. Splines (184) extend axially along and are arranged circumferentially about waveguide (180) at the acoustic node, and may be provided in any suitable quantity and circumferential arrangement. Circumferential projection (186) extends circumferentially about waveguide (180), through axial medial portions of splines (184) so as to interconnect splines (184). In the present example, circumferential projection (186) extends continuously about an outer circumference of waveguide (180) at the acoustic node so as to define an annular structure. In other examples, circumferential projection (186) may comprise a plurality of disconnected circumferential segments.

As shown in FIG. 19, torque transfer collar (190) includes a first collar half (192) and a second collar half (194) pivotably coupled together at a hinge (196) extending axially along lower portions of collar halves (192, 194), thereby providing collar (190) with a clam shell-like configuration. Collar halves (192, 194) are pivotable relative to one another between an open position (shown in FIG. 19) and a closed position (not shown) for coupling to waveguide (180). Collar halves (192, 194) may be constrained in the closed position by a variety of suitable fastening or latching mechanisms readily apparent to those of ordinary skill in the art. Each collar half (192, 194) includes a semi-cylindrical body portion (198) and a tab-like lug (200) projecting radially outwardly from body portion (198). Lugs (200) are arranged to be diametrically opposed to one another when first and second collar halves (192, 194) are closed about waveguide (180). Lugs (200) are configured to secure collar (190) rotationally and axially relative to rotation knob (46), as well as rotationally relative to outer and inner tubes (34, 36), similar to lugs (56) described above.

An interior of each collar half (192, 194) includes a plurality of axially extending slots (202) configured to receive splines (184) of waveguide (180), and thereby secure torque transfer collar (190) rotationally relative to waveguide (180) when collar (190) is clamped about waveguide (180). The interior of each collar half (192, 194) further includes a circumferential slot (204) extending circumferentially about the interior and through axial medial portions of axial slots (202). Circumferential slots (204) cooperate to receive circumferential projection (186) of waveguide (180) and thereby secure torque transfer collar (190) axially relative to waveguide (180). In that regard, circumferential slot (204) includes a proximal slot side defined by distally facing surfaces of the surrounding structure of body portion (198) through which circumferential slot (204) extends, and an opposed distal slot side defined by proximally facing surfaces of the surrounding structure of body portion (198) through which circumferential slot (204) extends. When torque transfer collar (190) is clamped about the nodal coupling feature of waveguide (180), a proximal side of circumferential projection (186) abuts the proximal slot sides of circumferential slots (204), and a distal side of circumferential projection (186) abuts the distal slot sides of circumferential slots (204), thereby securing collar (190) axially relative to waveguide (180).

Figure 20:
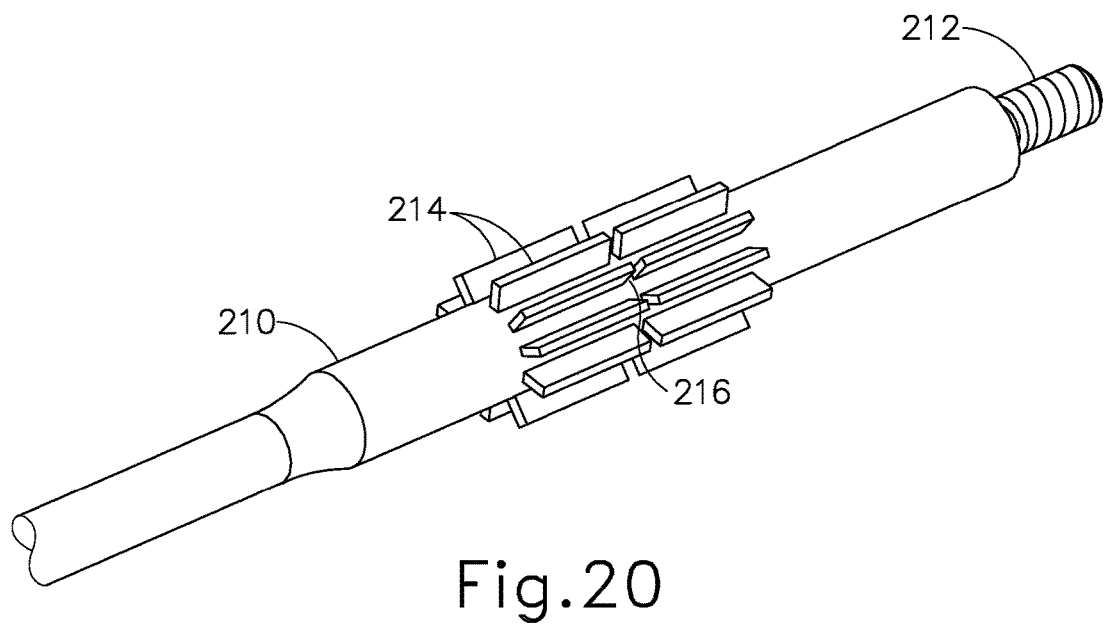
FIG. 20 depicts a perspective view of a proximal portion of another exemplary waveguide.
Figure 21:
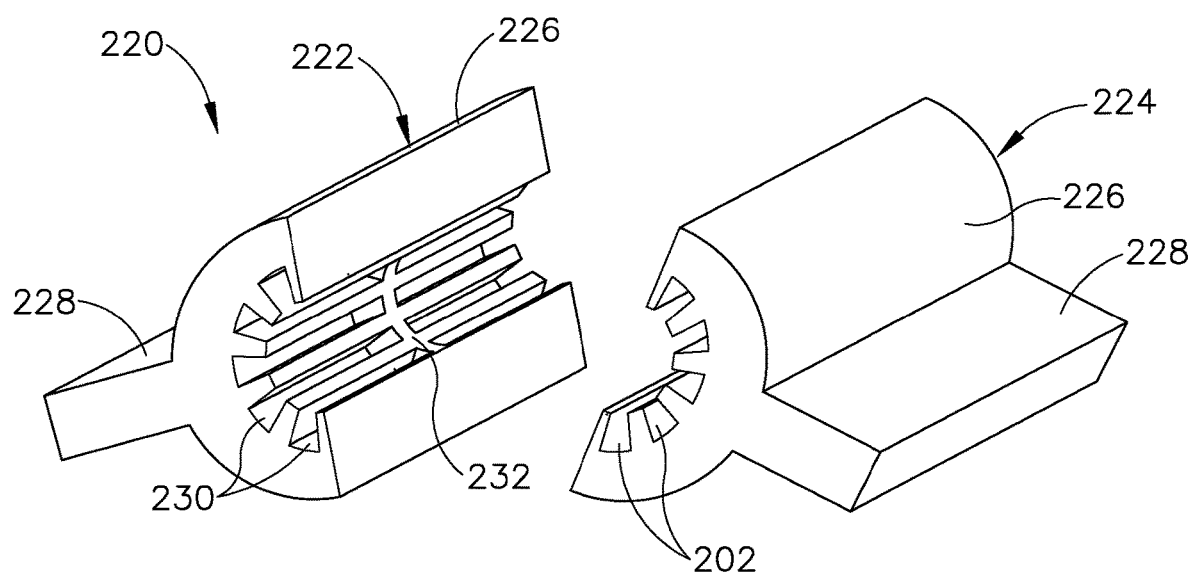
FIG. 21 depicts a torque transfer collar configured for use with the waveguide of FIG. 20, showing first and second components of the torque transfer collar configured to couple together.

H. Exemplary Waveguide Having Circumferential Slot and Torque Transfer Collar Having Circumferential Projection FIGS. 20 and 21 show another exemplary waveguide (210) and a corresponding torque transfer collar (220) suitable for use in ultrasonic surgical instrument (10). As shown in FIG. 20, waveguide (210) is similar to waveguide (180) described above in that waveguide (210) includes a threaded proximal end (212) configured to threadedly couple with a distal end of ultrasonic transducer (26), and waveguide (180) is configured to communicate ultrasonic energy from transducer (26) to ultrasonic blade (28). A radially enlarged proximal portion of waveguide (210) includes a nodal coupling feature in the form of a plurality of splines (214) and a circumferential slot (216) extending through axial medial ports of splines (214) at an acoustic node of waveguide (210). Splines (214) extend axially along and are arranged circumferentially about waveguide (210) at the acoustic node, and may be provided in any suitable quantity and circumferential arrangement.

As shown in FIG. 21, torque transfer collar (220) is similar to torque transfer collar (190) described above in that collar (220) includes a first collar half (222) and a second collar half (224) configured to couple together about splines (214) of waveguide (210). Though not shown, collar halves (222, 224) may be pivotably coupled in a manner similar to collar halves (192, 194) of collar (190) described above to provide collar (220) with a clam shell-like configuration. Collar halves (222, 224) may be coupled together with a variety of suitable mechanisms as will be readily apparent to persons of ordinary skill in the art. Each collar half (192, 194) includes a semi-cylindrical body portion (226) and a tab-like lug (228) projecting radially outwardly from body portion (226). Lugs (228) are arranged to be diametrically opposed to one another when first and second collar halves (222, 224) are closed about waveguide (210). Lugs (228) are configured to secure collar (220) rotationally and axially relative to rotation knob (46), as well as rotationally relative to outer and inner tubes (34, 36), similar to lugs (56) described above.

An interior of each collar half (222, 224) includes a plurality of axially extending slots (230) configured to receive splines (214) of waveguide (210), and thereby secure torque transfer collar (220) rotationally relative to waveguide (210) when collar (220) is clamped about waveguide (210). The interior of each collar half (222, 224) further includes a circumferential projection (232) extending radially inwardly toward a central axis of collar (220) and through axial medial portions of axial slots (230). In the present example, circumferential projections (232) cooperate to extend continuously about a central axis of collar (220) when collar halves (222, 224) are clamped together. In other examples, each circumferential projection (232) may comprise a plurality of disconnected circumferential segments.

Circumferential projections (232) of collar halves (222, 224) are configured to be received within circumferential slot (216) of waveguide (210) to thereby secure torque transfer collar (220) axially relative to waveguide (210). In that regard, circumferential slot (216) includes a proximal slot side defined by distally facing surfaces of proximal portions of splines (214), and an opposed distal slot side defined by proximally facing surfaces of distal portions of splines (214). When torque transfer collar (220) is clamped about the nodal coupling feature of waveguide (210), proximal sides of circumferential projections (232) abut the proximal slot side of circumferential slot (216), and distal sides of circumferential projections (232) abut the distal slot side of circumferential slot (216), thereby securing collar (220) axially relative to waveguide (210).

Figure 22:
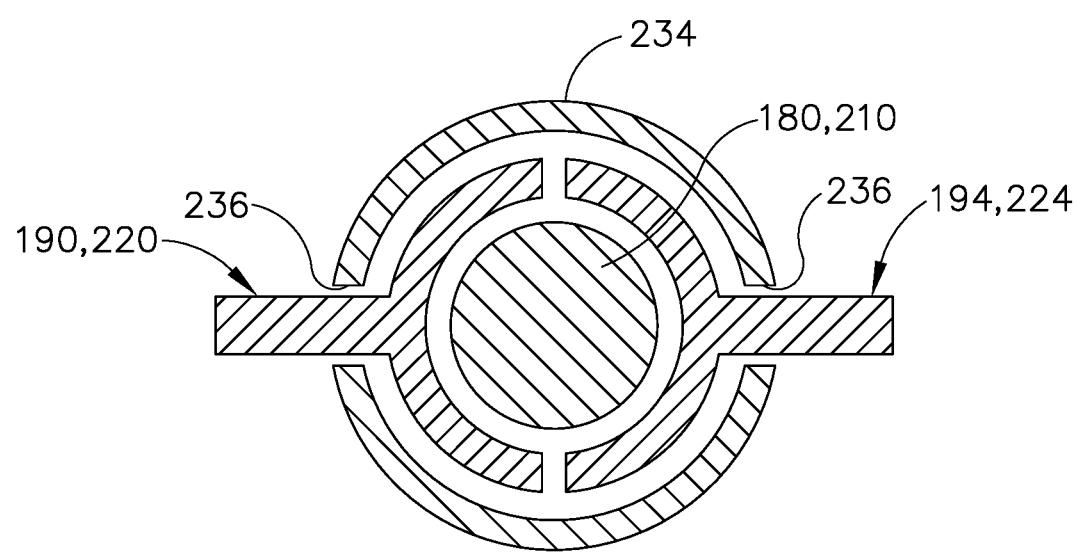
FIG. 22 depicts a schematic end sectional view of the waveguides of FIGS. 18 and 20 in combination with their respective torque transfer collars of FIGS. 19 and 21, showing the assembly encircled by a tube of a shaft assembly.

FIG. 22 schematically shows waveguides (180, 210) and torque transfer collars (190, 220) of FIGS. 18-21, described above, in combination with an exemplary annular structure (234) configured to engage outer surfaces of collar halves (192, 194, 222, 224) to thereby maintain collar halves (192, 194, 222, 224) in a closed configuration about waveguides (180, 210). In some examples, annular structure (234) may be in the form of inner tube (36). In other examples, annular structure (234) may be provided in addition to inner tube (36) and arranged radially inwardly thereof. In either case, annular structure (234) includes a pair of opposed axially extending slots (236) configured to receive lugs (200, 228) therethrough to enable lugs (200, 228) to couple with rotation knob (46).

Figure 23:
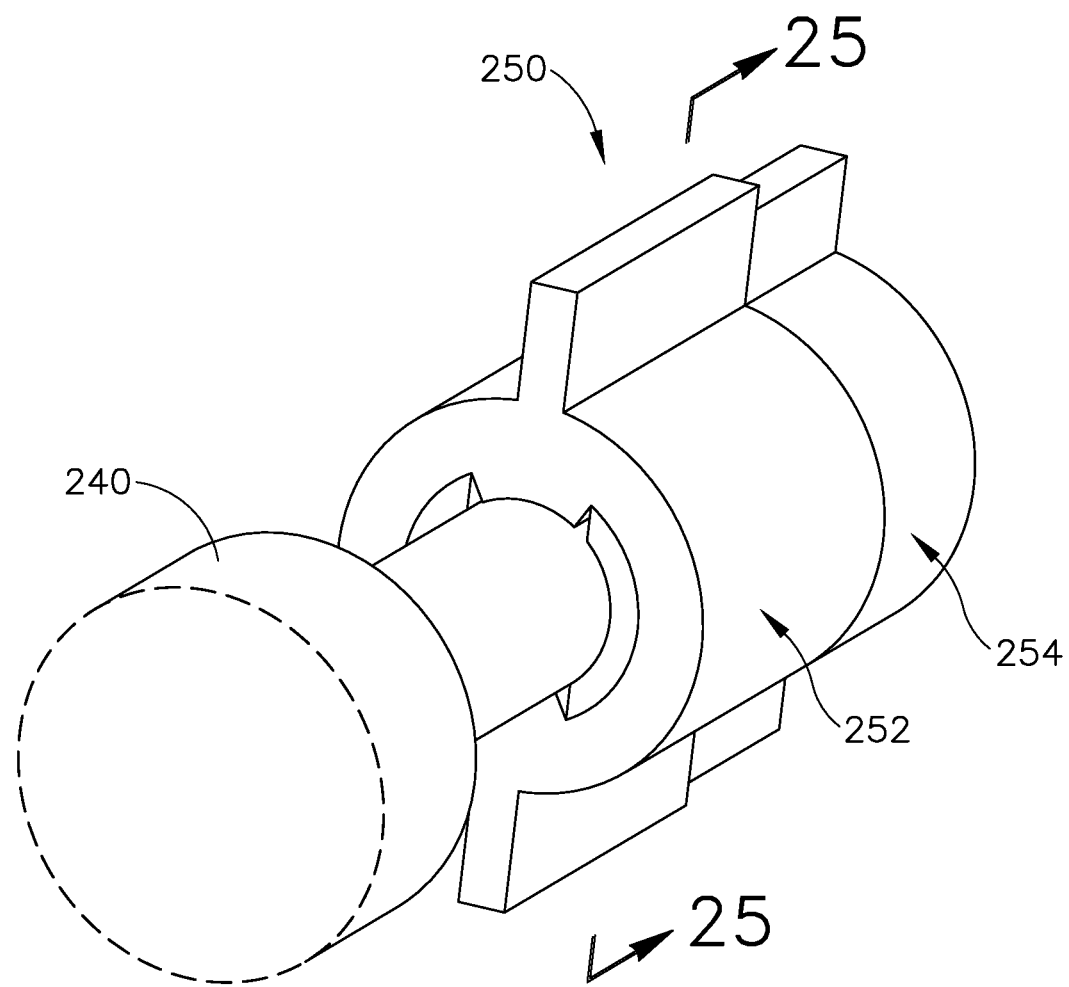
FIG. 23 depicts a schematic perspective view of another exemplary torque transfer collar having proximal and distal collar components coupled together, showing the torque transfer collar mounted to a proximal portion of a waveguide.
Figure 24:
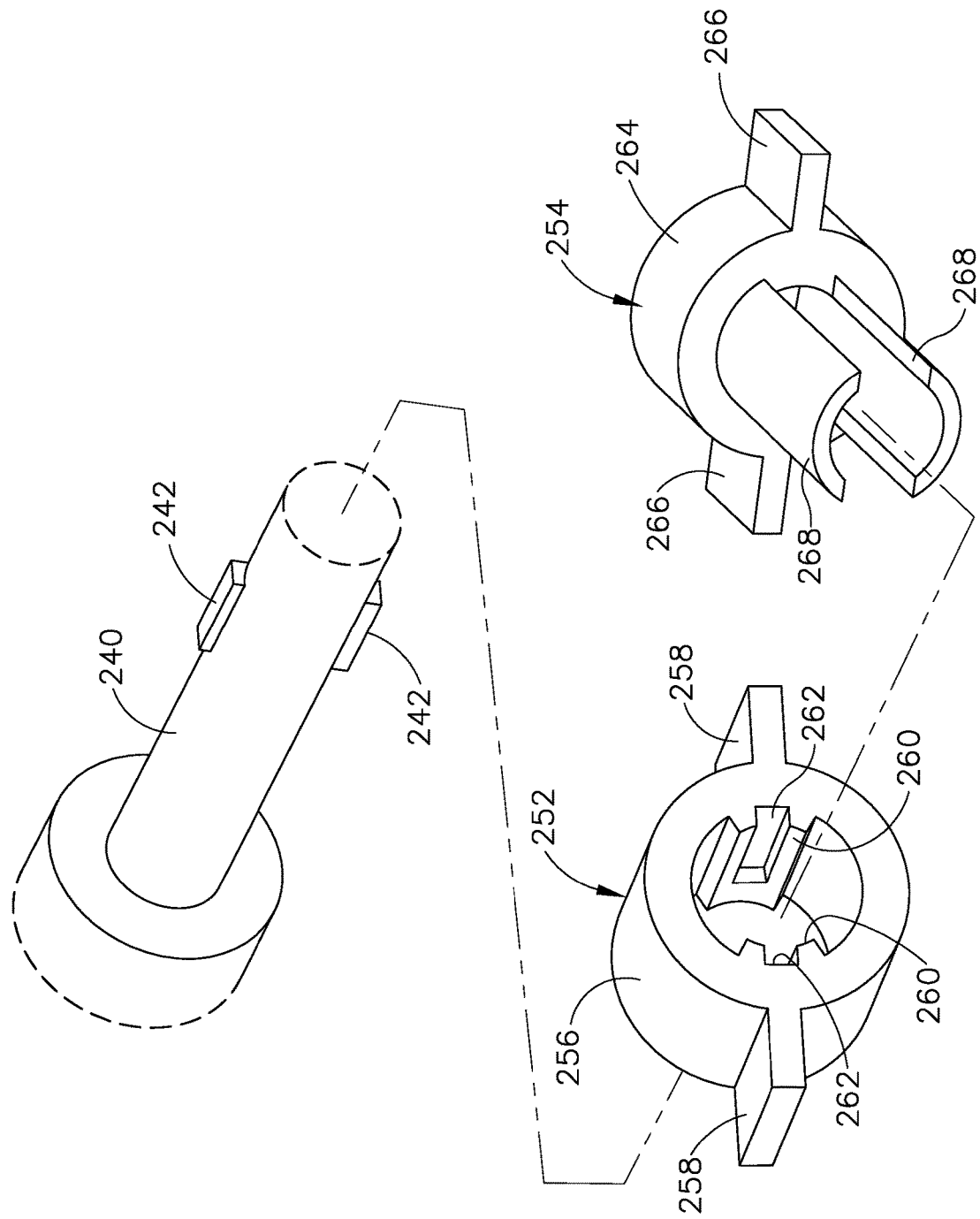
FIG. 24 depicts a disassembled perspective view of the torque transfer collar components and waveguide of FIG. 23.
Figure 25:
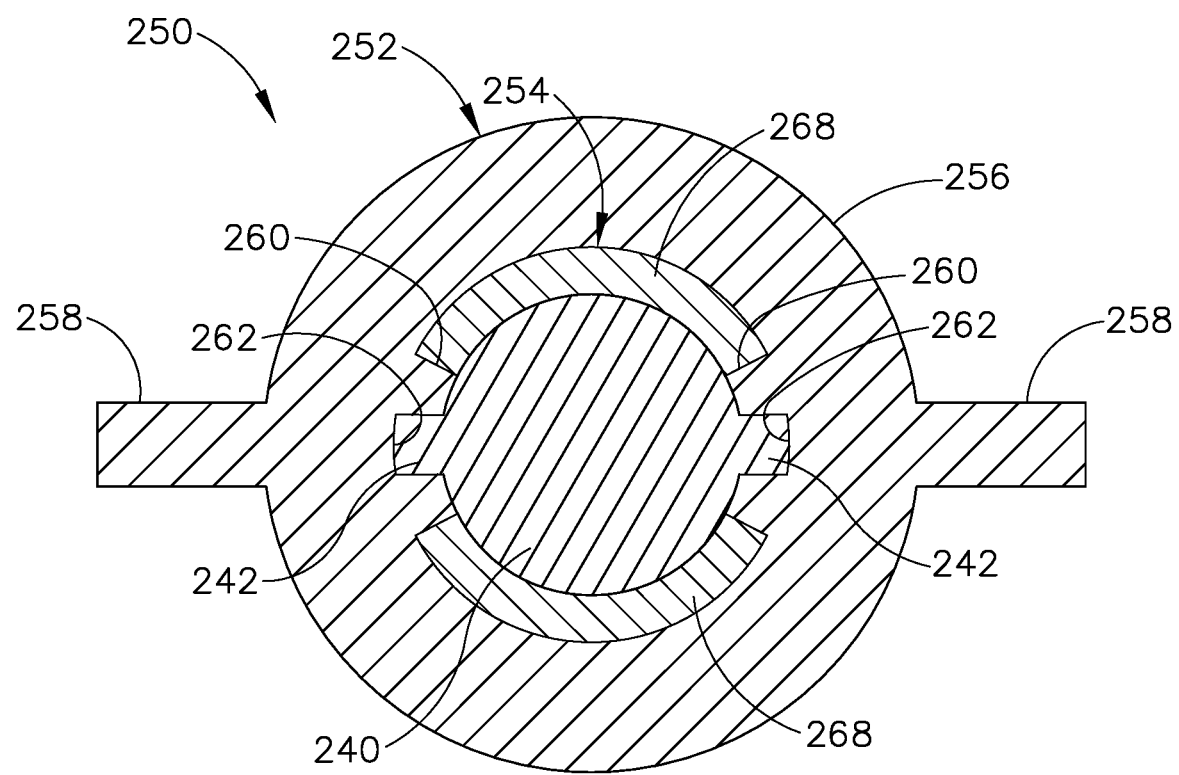
FIG. 25 depicts an end sectional view taken along section line 25-25 in FIG. 23, showing coupling of the torque transfer collar components and the waveguide.

I. Exemplary Waveguide and Torque Transfer Collar Having Proximal and Distal Collar Components FIGS. 23-25 show another exemplary waveguide (240) and a corresponding torque transfer collar (250) suitable for use in ultrasonic surgical instrument (10). Waveguide (240) is similar to waveguide (40) described above in that a proximal end (not shown) of waveguide (240) is configured to acoustically couple with ultrasonic transducer (26), and waveguide (240) is configured to communicate ultrasonic energy from transducer (26) to ultrasonic blade (28) via a distal end (not shown) of waveguide (240). As best seen in FIG. 24, a proximal portion of waveguide (240) includes a nodal coupling feature in the form of a pair of axial projections (242) extending radially outwardly from waveguide (240) at an acoustic node thereof. In the present example, axial projections (242) are arranged at diametrically opposed positions on waveguide (240), though it will be appreciated that axial projections (242) may be provided in various other suitable quantities and circumferential arrangements in other examples.

As shown in FIGS. 23-25, torque transfer collar (250) includes a proximal collar component (252) and a distal collar component (254). Each collar component (252, 254) is configured to encircle waveguide (240) and interlock coaxially with the adjacent collar component (252, 254) to capture axial projections (242) of waveguide (240) between collar components (252, 254) and thereby secure torque transfer collar (250) rotationally and axially relative to waveguide (240). Proximal collar component (252) includes a cylindrical, annular proximal body portion (256) and a pair of proximal lugs (258) extending radially outwardly from proximal body portion (256) at diametrically opposed positions. An interior of proximal collar component (252) includes an opposed pair of U-shaped projections (260) aligned radially with proximal lugs (258). Each U-shaped projection (260) extends radially inwardly and defines an axial slot (262) having a closed proximal end and an open distal end opening to a distal end of proximal collar component (252). As described below, each axial slot (262) is configured to receive a respective axial projection (242) of waveguide (240).

Distal collar component (254) includes a cylindrical, annular distal body portion (264) and a pair of distal lugs (266) extending radially outwardly from distal body portion (264) at diametrically opposed positions. Distal collar component (254) further includes a pair of opposed locking legs (268) extending proximally from a proximal end of distal body portion (264). Each locking leg (268) is an elongate structure having an arcuate transverse cross-section that extends circumferentially along a respective portion of an inner circumference of distal body portion (264). Locking legs (268) are spaced apart from one another by circumferential gaps configured to receive U-shaped projections (260) of proximal collar component (252), as shown in FIG. 25. Locking legs (268) are configured to lockingly engage proximal collar component (252) with a press-fit or a snap-fit engagement, for example, to thereby couple distal collar component (254) with proximal collar component (252). Further, proximal and distal collar components (252, 254) are configured to assemble with waveguide (240) to form the coaxial configuration shown in FIG. 25.

FIGS. 26A-26D show steps of an exemplary method for coupling proximal and distal collar components (252, 254) of torque transfer collar (250) with waveguide (240) and with one another. The coupling features of collar components (252, 254) and waveguide (240) are shown in a planar (or "unrolled") form to provide enhanced visibility of interaction between the coupling features. In that regard, FIGS. 26A-26D may be viewed in combination with FIGS. 23-25 to appreciate the interaction of the coupling features in three-dimensional space.

Figure 26A:
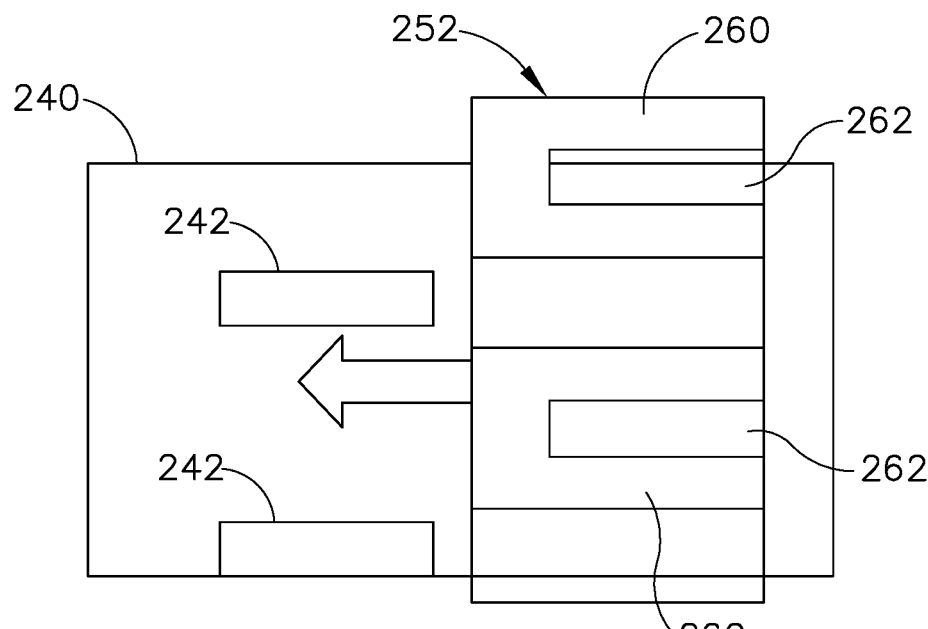
FIG. 26A depicts a schematic view of the proximal collar component and the waveguide of FIG. 23, showing the proximal collar component in a first rotational orientation and being advanced proximally over the waveguide.
Figure 26B:
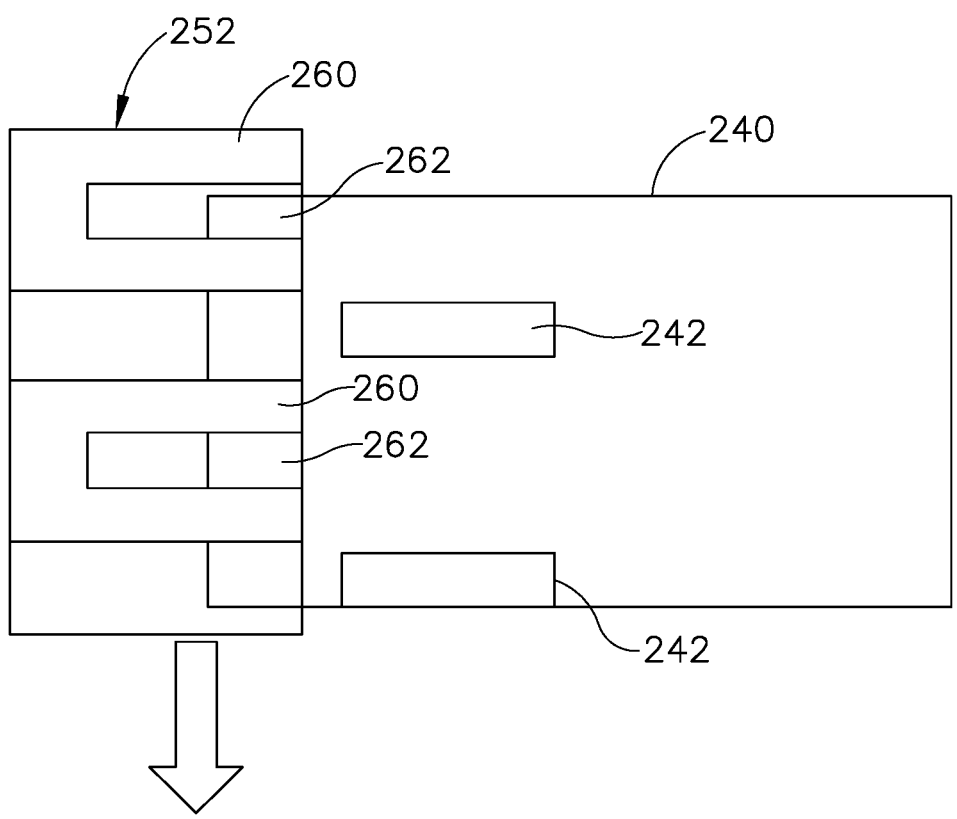
FIG. 26B depicts a schematic view of the proximal collar component and the waveguide of FIG. 26A, showing the proximal collar component positioned proximally of projections of the waveguide and being rotated to a second rotational orientation.

FIG. 26A shows a first step of the exemplary coupling method in which proximal collar component (252) is advanced proximally over waveguide (240). Proximal collar component (252) is maintained in a first rotational orientation relative to waveguide (240) such that U-shaped projections (260) of proximal collar component (252) are aligned with circumferential gaps extending between axial projections (242) of waveguide (240). This orientation enables proximal collar component (252) to be advanced proximally beyond axial projections (242), as shown in FIG. 26B. As shown in FIG. 26B, proximal collar component (252) is then rotated about waveguide (240) toward a second rotational orientation in which axial slots (262) of U-shaped projections (260) align with axial projections (242) of waveguide (240).

Figure 26C:
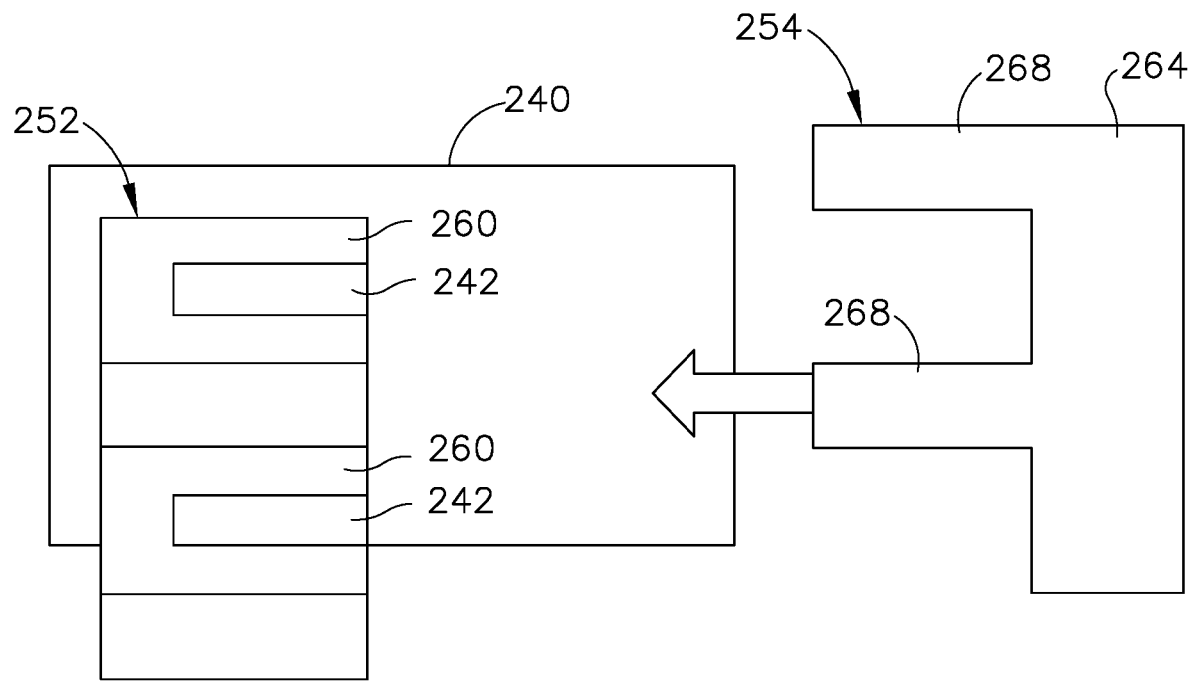
FIG. 26C depicts a schematic view of the proximal collar component and the waveguide of FIG. 26B, showing the proximal collar component in the second rotational orientation and in a distal position in which it engages the waveguide projections, additionally showing proximal application of the distal collar component of FIG. 23.
Figure 26D:
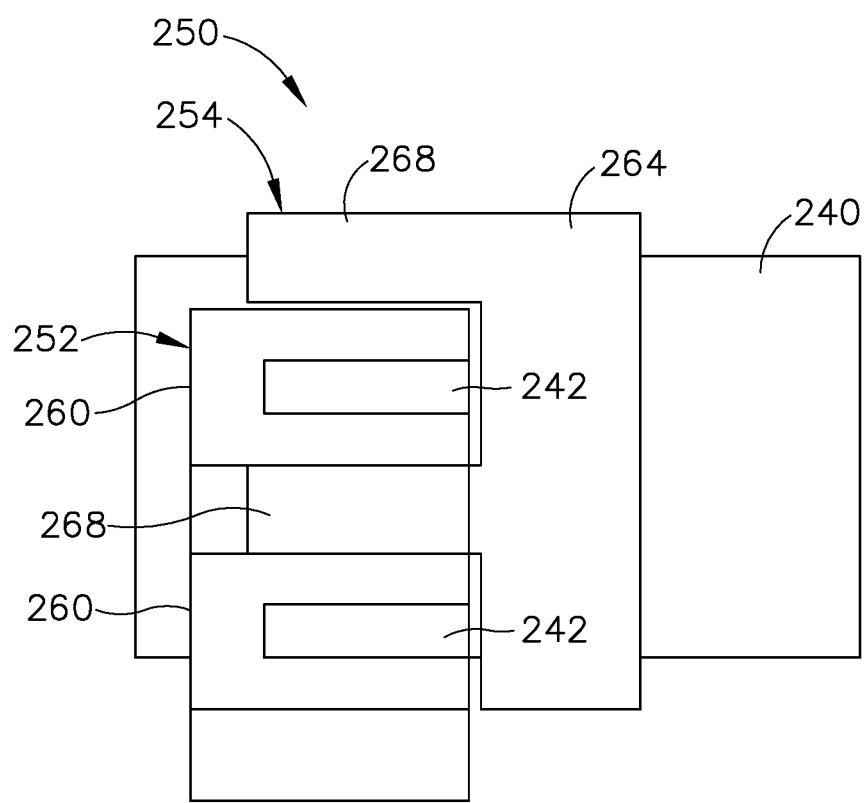
FIG. 26D depicts a schematic view of the proximal collar component, the distal collar component, and the waveguide of FIG. 26C, showing the distal collar component in a proximal position in which it couples with the proximal collar component to thereby secure the waveguide axially relative to the torque transfer collar.

As shown in FIG. 26C, proximal collar component (252) is then advanced distally, while remaining in the second rotational orientation, so that waveguide projections (242) are received within axial slots (262) of proximal collar component (252). Distal collar component (254) is then advanced proximally over waveguide (240) so that locking legs (268) are received radially inward of proximal body portion (256) of proximal collar component (252) and within circumferential gaps formed between U-shaped projections (260), as shown in FIGS. 26C and 26D, as well as FIG. 25. In this final configuration, locking legs (268) lockingly engage proximal collar component (252) as described above, and collar components (252, 254) engage waveguide projections (242) so that torque transfer collar (250) is constrained rotationally and axially relative to waveguide (240). In particular, as shown in FIG. 26D, elongate sides of U-shaped projections (260) abut elongate sides of waveguide projections (242) to fix collar (250) rotationally. Additionally, closed proximal ends of U-shaped projections (260) abut proximal ends of waveguide projections (242), and distal body portion (264) of distal collar component (254) abuts distal ends of waveguide projections (242), thereby fixing collar (250) axially relative to waveguide (240).

Figure 27A:
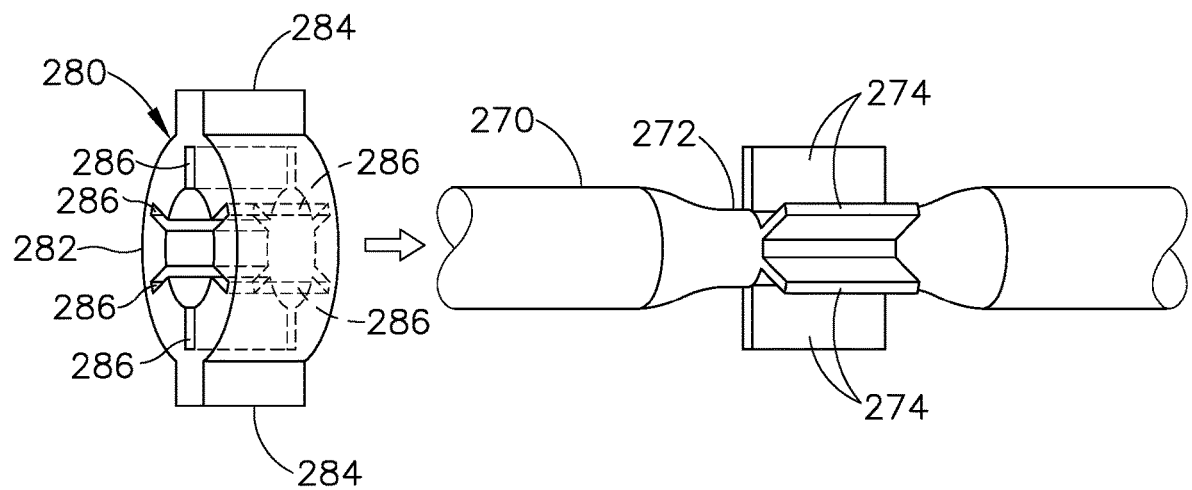
FIG. 27A depicts a disassembled side elevational view of another exemplary torque transfer collar and a waveguide.
Figure 27B:
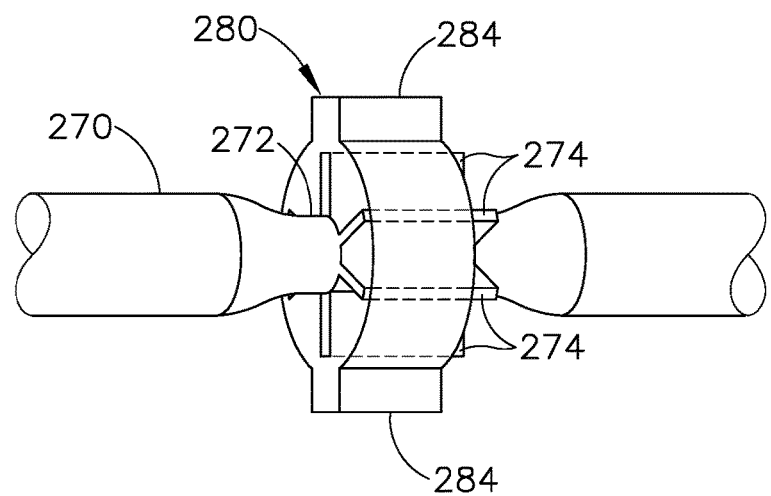
FIG. 27B depicts an assembled side elevational view of the torque transfer collar and the waveguide of FIG. 27A.

J. Exemplary Torque Transfer Collar and Waveguide Having Splines with Shaped Ends FIGS. 27A and 27B show another exemplary waveguide (270) and a corresponding torque transfer collar (280) suitable for use in ultrasonic surgical instrument (10). Waveguide (270) is similar to waveguide (40) described above in that a proximal end (not shown) of waveguide (270) is configured to acoustically couple with ultrasonic transducer (26), and waveguide (270) is configured to communicate ultrasonic energy from transducer (26) to ultrasonic blade (28). Waveguide (270) includes a narrowed proximal portion (272) formed at a proximal acoustic node thereof, and a nodal coupling feature in the form of splines (274) that project radially outwardly from narrowed proximal portion (272). Splines (274) are arranged circumferentially about waveguide (270) at the proximal acoustic node, and may be provided in any suitable quantity and circumferential arrangement.

Torque transfer collar (280) includes an annular collar body (282) configured to encircle narrowed proximal portion (272) of waveguide (270), and a pair of tab-like lugs (284) extending radially outwardly from collar body (282) at diametrically opposed positions. Lugs (284) are configured to secure collar (280) rotationally and axially relative to rotation knob (46), as well as rotationally relative to outer and inner tubes (34, 36), similar to lugs (56) described above. An interior of collar (280) includes a plurality of axially extending slots (286) arranged circumferentially about the interior and configured to receive splines (274) therein, as shown in FIG. 27B, for example with an interference-fit engagement. As shown in FIG. 27B, collar (280) is advanced over waveguide (270) in a distal to proximal direction, and collar (280) is positioned over splines (274) such that distal ends of splines (274) are received within axial slots (286) and proximal ends of splines (274) extend proximally beyond axial slots (286) and a proximal end of collar (280).

As shown in FIGS. 28A-29B, described below, the exposed proximal ends of splines (274) may be shaped in various manners configured to interfere with slots (286) to thereby constrain collar (280) axially relative to waveguide (270). FIGS. 28A and 28B show a first exemplary configuration in which the proximal end of each spline (274) is altered to include a bulbous protrusion (288). By way of example only, bulbous protrusion (288) may be formed by deforming the proximal end of spline (274) mechanically or thermally, for example with a laser or other suitable heat source. FIGS. 29A and 29B show a second exemplary configuration in which the proximal end of each spline (274) is deformed mechanically to include a bent corner (290). Bulbous protrusion (288) and bent corner (290) each provide a distally facing surface configured to abut a proximal end of torque transfer collar (280), or otherwise interfere with a proximal end of the respective axial slot (286), to thereby constrain torque transfer collar (280) axially relative to waveguide (270). Various other suitable configurations for proximal ends of splines (274) will be readily apparent to those of ordinary skill in the art.

K. Exemplary Rotation Knobs Configured to Permit Axial Translation of Waveguide and Torque Transfer Collar Relative to Knob Ultrasonic surgical instrument (10) may be exposed to various situations during use in which instrument (10) is unintentionally dropped from an elevated position. The resulting impact force absorbed by the instrument (10) as it hits the ground surface may force its waveguide, and the torque transfer collar coupled axially to the waveguide, proximally toward rotation knob (46) and handle assembly (12). Such sudden and forceful translation of the waveguide and torque transfer collar relative to rotation knob (46) may cause the lugs of the torque transfer collar to shear off inside of rotation knob (46). This results in rotational decoupling of rotation knob (46) and the waveguide, thereby rendering surgical instrument (10) unusable. For example, the user is no longer able to manipulate the rotational orientation of the waveguide and its ultrasonic blade relative to handle assembly (12), nor is the user able to easily rotationally decouple the waveguide from ultrasonic transducer (26). The exemplary rotation knobs described below in connection with FIGS. 30-34 enable at least some axial translation of the waveguide and its torque transfer collar relative to handle assembly (12) to minimize the risk of collar lugs shearing during an unintentional drop of surgical instrument (10).

Figure 30:
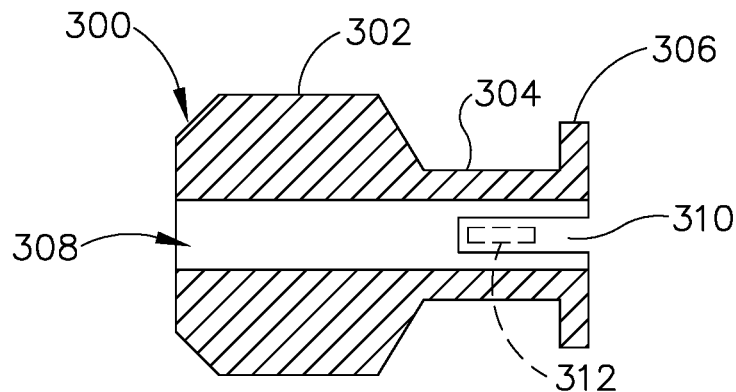
FIG. 30 depicts a side sectional view of an exemplary rotation knob having an elongate slot configured to receive a side lug of a torque transfer collar therethrough.

FIG. 30 shows an exemplary rotation knob (300) suitable for use with ultrasonic surgical instrument (10), in place of rotation knob (46). Rotation knob (300) includes a distal gripping portion (302), a shaft portion (304) extending proximally from gripping portion (302), a flange (306) projecting from shaft portion (304) and configured to rotatably couple rotation knob (300) with handle assembly (12), and a central bore (308) configured to receive shaft assembly (14) therethrough. Unlike rotation knob (46), rotation knob (300) includes a pair of opposed elongate slots (310) extending axially through shaft portion (304). Each elongate slot (310) has a closed distal end and an open proximal end that opens to a proximal end of rotation knob (300). Each elongate slot (310) is configured to receive a respective lug (312) of a torque transfer collar (not shown), such as any of the exemplary torque transfer collars described above, and permit lug (312) to translate axially within elongate slot (310). This configuration enables the torque transfer collar and its lugs (312), as well as the waveguide (not shown) to which the collar is axially coupled, to translate proximally relative to rotation knob (300) and handle assembly (12), for example when surgical instrument (10) is dropped, while maintaining the torque transfer collar and waveguide in rotational engagement with rotation knob (300).

Figure 31:
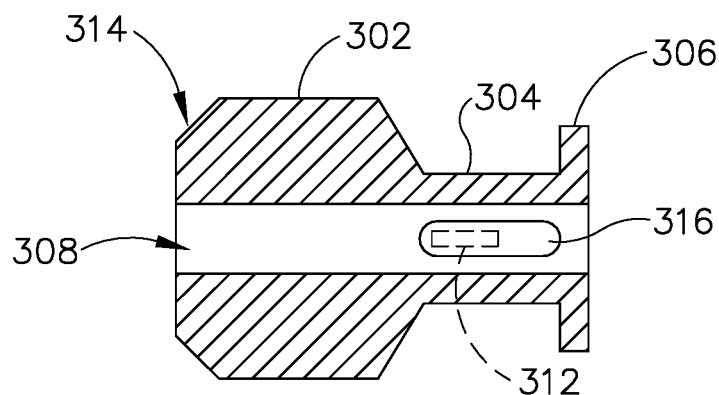
FIG. 31 depicts a side sectional view of another exemplary rotation knob having an elongate slot configured to receive a side lug of a torque transfer collar therethrough.

FIG. 31 shows another exemplary rotation knob (314) suitable for use with ultrasonic surgical instrument (10), in place of rotation knob (46). Rotation knob (314) is similar to rotation knob (300), as indicated by like reference numerals, except that rotation knob (314) includes a pair of elongate slots (316) each having closed, rounded proximal and distal ends.

Figure 32:
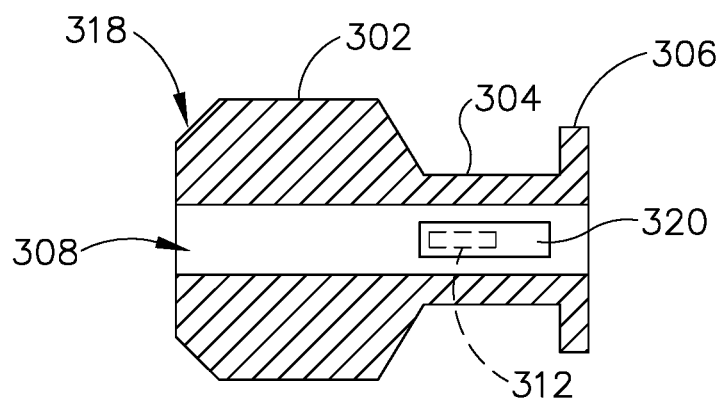
FIG. 32 depicts a side sectional view of another exemplary rotation knob having an elongate slot configured to receive a side lug of a torque transfer collar therethrough.

FIG. 32 shows another exemplary rotation knob (318) suitable for use with ultrasonic surgical instrument (10), in place of rotation knob (46). Rotation knob (318) is similar to rotation knob (314), as indicated by like reference numerals, except that rotation knob (318) includes a pair of elongate slots (320) each having closed, rectangular proximal and distal ends.

Figure 33:
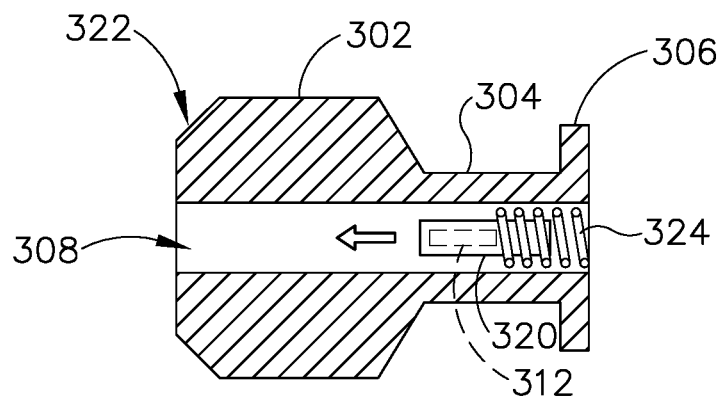
FIG. 33 depicts side sectional view of another exemplary rotation knob having an elongate slot configured to receive a side lug of a torque transfer collar therethrough, and a resilient member positioned according to a first exemplary configuration.

FIG. 33 shows another exemplary rotation knob (322) suitable for use with ultrasonic surgical instrument (10), in place of rotation knob (46). Rotation knob (322) is similar to rotation knob (318), as indicated by like reference numerals, except as otherwise described. In particular, rotation knob (322) includes one or more resilient members (324) configured to contact and resiliently bias torque transfer collar lugs (312) toward closed distal ends of elongate slots (320). In the present example, resilient members (324) are shown in the form of compression springs, though various other types of resilient members may be employed. Upon an impact of ultrasonic surgical instrument (10) against a ground surface, resilient members (324) are configured to resiliently deform (e.g., by compressing) and thereby absorb proximally directed impact forces exerted on the waveguide and its torque transfer collar. Advantageously, this configuration further minimizes the risk of shearing of collar lugs (312) during an unintentional drop of surgical instrument (10).

Figure 34:
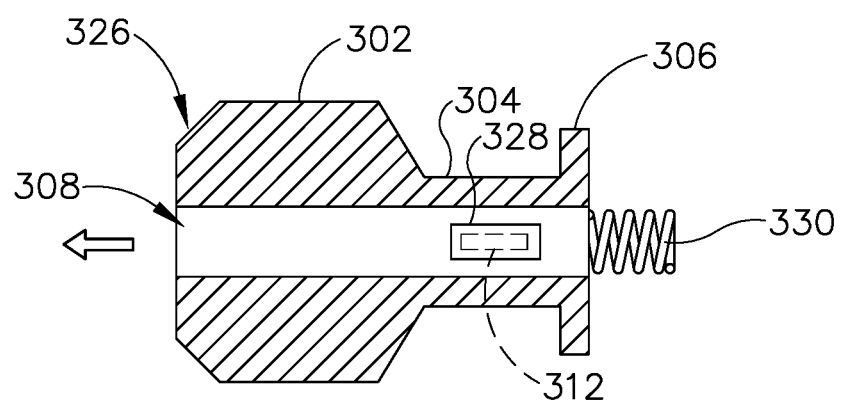
FIG. 34 depicts a side sectional view of another exemplary rotation knob having a slot configured to receive a side lug of a torque transfer collar therethrough, and a resilient member positioned according to a second exemplary configuration.

FIG. 34 shows another exemplary rotation knob (326) suitable for use with ultrasonic surgical instrument (10), in place of rotation knob (46). Rotation knob (326) is similar to rotation knob (322), as indicated by like reference numerals, except as otherwise described. In particular, rotation knob (322) includes slots (328) that are sized and shaped to receive torque transfer collar lugs (312) without permitting axial translation of lugs (312) within slots (328). Instead, rotation knob (326) itself is configured to translate axially relative to handle assembly (12) to thereby permit axial translation of the waveguide and its torque transfer collar relative handle assembly (12). Additionally, a proximal end of rotation knob (326) is coupled to a resilient member (330), shown in the form of a compression spring. Resilient member (330) is configured to resiliently bias rotation knob and at least the waveguide and its torque transfer collar of the shaft assembly (14) distally. Similar to resilient members (324) described above, resilient member (330) is configured to resiliently deform (e.g., by compressing) and thereby absorb proximally directed impact forces exerted on the waveguide and its torque transfer collar when surgical instrument (10) impacts a ground surface during an unintentional drop.

Figure 35:
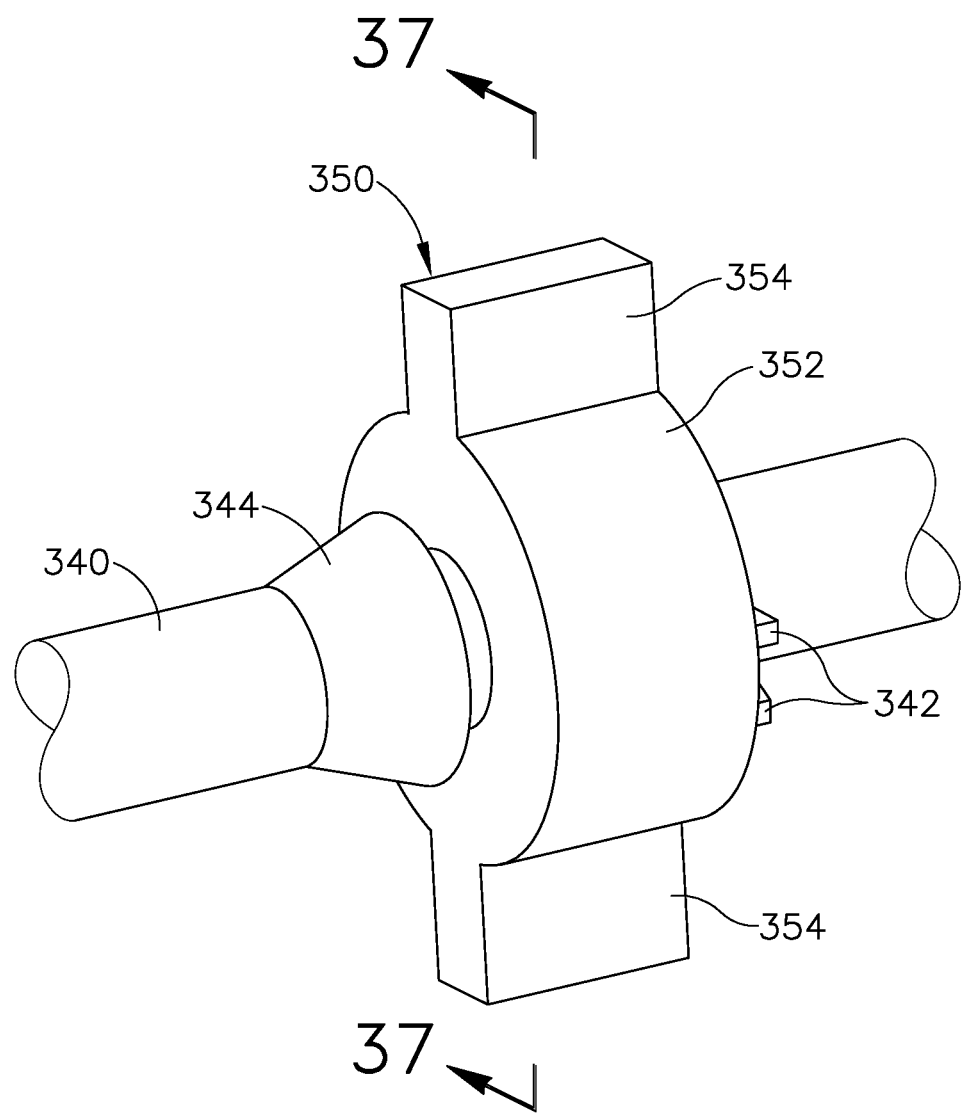
FIG. 35 depicts a perspective view of another exemplary torque transfer collar and a waveguide.
Figure 36:
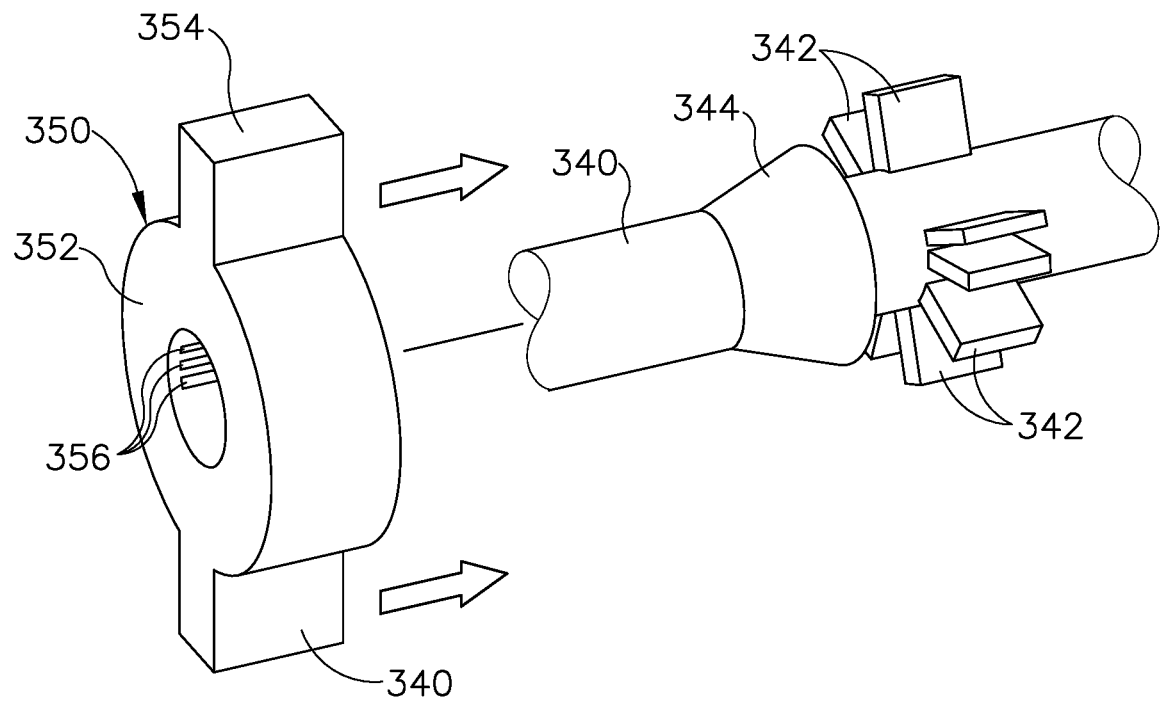
FIG. 36 depicts a disassembled perspective view of the torque transfer collar and the waveguide of FIG. 35.
Figure 37:
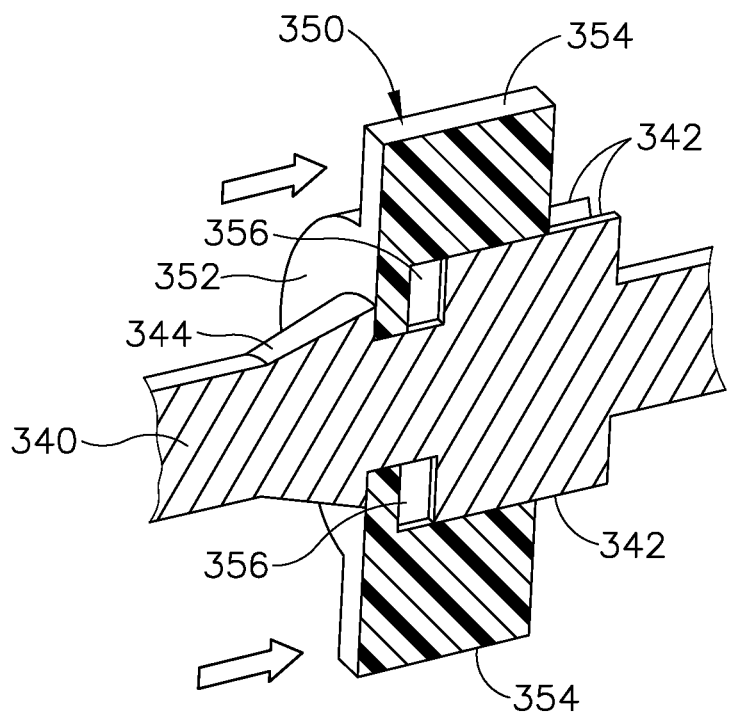
FIG. 37 depicts a perspective sectional view taken along section line 37-37 of FIG. 35, showing additional details of the torque transfer collar and the waveguide.

M. Exemplary Waveguide Having Flange and Torque Transfer Collar Configured to Permit Relative Axial Movement Therebetween FIGS. 35-37 show another exemplary waveguide (340) and a corresponding torque transfer collar (350) suitable for use in ultrasonic surgical instrument (10). Waveguide (340) is similar to waveguide (40) described above in that a proximal end (not shown) of waveguide (340) is configured to acoustically couple with ultrasonic transducer (26), and waveguide (340) is configured to communicate ultrasonic energy from transducer (26) to ultrasonic blade (28). As best seen in FIG. 36, a proximal portion of waveguide (340) includes a nodal coupling feature in the form of a plurality of splines (342) and a tapered flange (344), each projecting radially outwardly from an outer surface of waveguide (340) at a proximal acoustic node thereof. In the present example, splines (342) are arranged circumferentially about waveguide (340) in first and second groups positioned in respective first and second diagonally opposed quadrants of a circular transverse cross-section of waveguide (340) at the acoustic node. This configuration provides a keying relationship between waveguide (340) and torque transfer collar (350). In other examples, splines (342) may be provided in various other suitable quantities and circumferential arrangements. Tapered flange (344) is arranged distally of splines (342) and tapers in a distal direction. As described below, tapered flange (344) promotes a snap-fit engagement between torque transfer collar (350) and waveguide (340).

As best shown in FIGS. 36 and 37, torque transfer collar (350) includes an annular collar body (352) configured to encircle waveguide (340), and a pair of tab-like lugs (354) extending radially outwardly from collar body (352) at diametrically opposed positions. Lugs (354) are configured to secure collar (350) rotationally and axially relative to rotation knob (46), as well as rotationally relative to outer and inner tubes (34, 36), similar to lugs (56) described above. An interior of collar (350) includes a plurality of axially extending slots (356) arranged circumferentially about the interior, and configured to receive splines (342) therein, as shown in FIG. 37, for example with an interference-fit engagement. Each axial slot (356) includes a closed proximal end spaced proximally from a proximal end of collar body (352), and an open distal end that opens to a distal end of collar body (352).

As shown in FIG. 36, torque transfer collar (350) is configured to be applied to waveguide (340) in a distal to proximal direction. Tapered flange (344) of waveguide (340) is formed with a maximum outer diameter at its proximal end that is greater than an inner diameter of collar body (352). Accordingly, torque transfer collar (350) must be forced proximally over tapered flange (344) such that collar (350) resiliently flexes and snaps over tapered flange (344), to the position shown in FIG. 37, such that collar (350) becomes coupled to waveguide (340) with a snap-fit engagement. As shown in FIG. 37, waveguide splines (342) are received within respective collar slots (356), and distal ends of splines (342) are configured to abut closed distal ends of slots (356) to thereby limit proximal motion of collar (350) relative to waveguide (340). Additionally, a distal end of collar body (352) is configured to abut a proximal face of tapered flange (344) to thereby limit distal motion of collar relative to waveguide (340). Accordingly, torque transfer collar (350) is constrained axially and rotationally relative to waveguide (340). However, whereas collar (350) is fixed rotationally relative to waveguide (340), collar (350) is permitted a slight range of axial motion relative to waveguide (340), as described below.

Figure 38A:
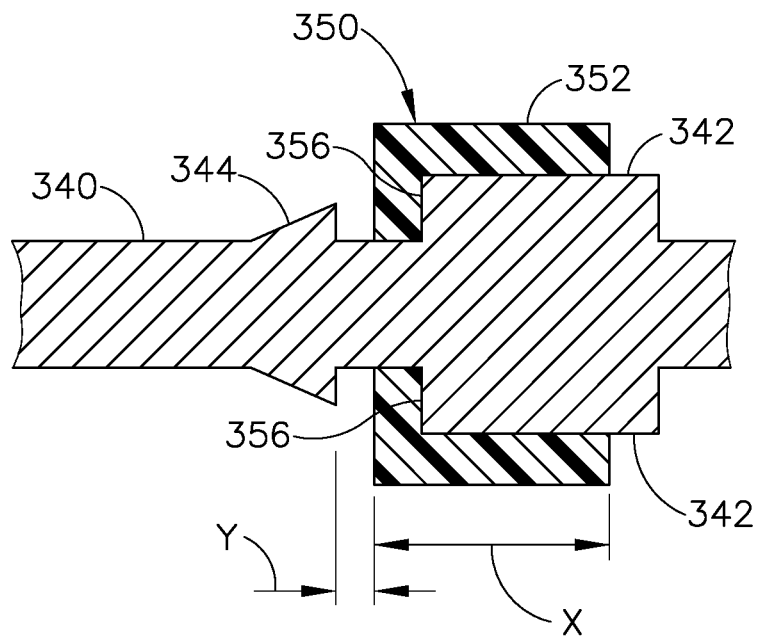
FIG. 38A depicts a side sectional view of the torque transfer collar and the waveguide of FIG. 35, showing the waveguide in a proximal position relative to the torque transfer collar.
Figure 38B:
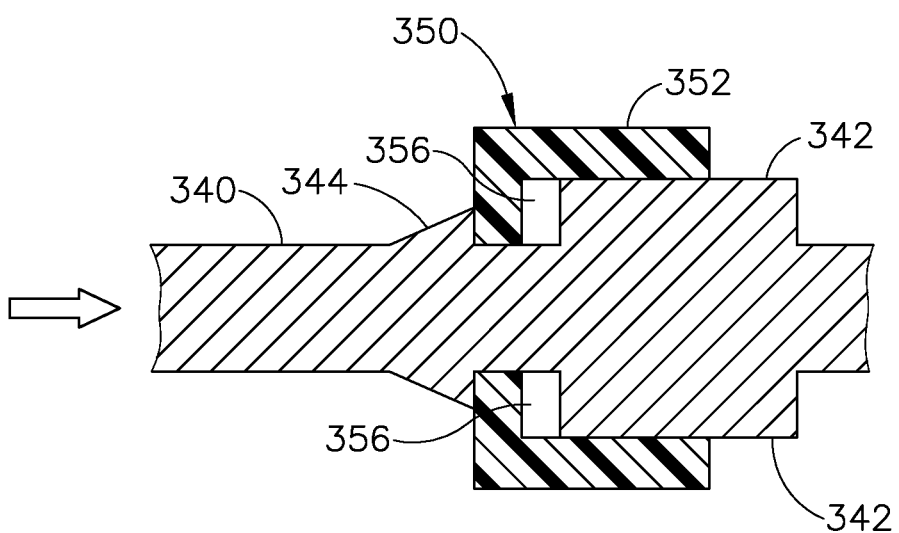
FIG. 38B depicts a side sectional view of the torque transfer collar and the waveguide of FIG. 38A, showing the waveguide in a distal position relative to the torque transfer collar.

As shown in FIG. 38A, each axial slot (356) of torque transfer collar (350) is formed with an axial slot length (X) that is greater than an axial gap length (Y) of an axial gap between distal ends of splines (342) and the proximal face of tapered flange (344). This configuration enables relative axial movement between waveguide (340) and torque transfer collar (350). In particular, waveguide (340) is configured to move axially relative to torque transfer collar (350) between a distal position shown in FIG. 38A in which splines (342) are fully seated against the closed proximal ends of collar slots (356), and a proximal position shown in FIG. 38B in which collar (350) abuts the proximal face of tapered flange (344). The ability of waveguide (340) to translate proximally relative to torque transfer collar (350) between the distal and proximal positions operates to at least partially dissipate a proximally directed impact force exerted on waveguide (340), for example during an unintended drop of ultrasonic surgical instrument (10) onto a ground surface. This translation and resulting dissipation of impact force advantageously minimizes the risk of collar lugs (354) shearing off within rotation knob (46), while ensuring that collar (350) remains rotationally and axially constrained relative to waveguide (340) to enable continued use of surgical instrument (10) following a drop.

Figure 39:
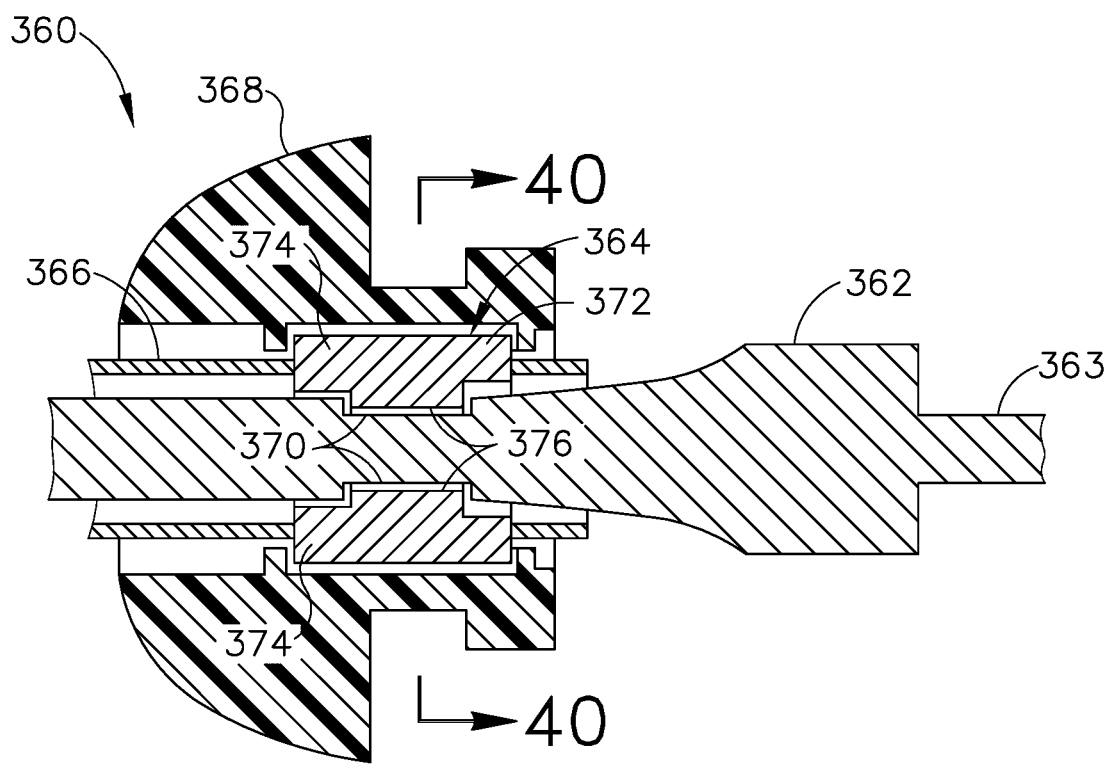
FIG. 39 depicts a side sectional view of another exemplary shaft assembly, a rotation knob, and a torque transfer collar rotationally coupling the shaft assembly with the rotation knob.
Figure 40:
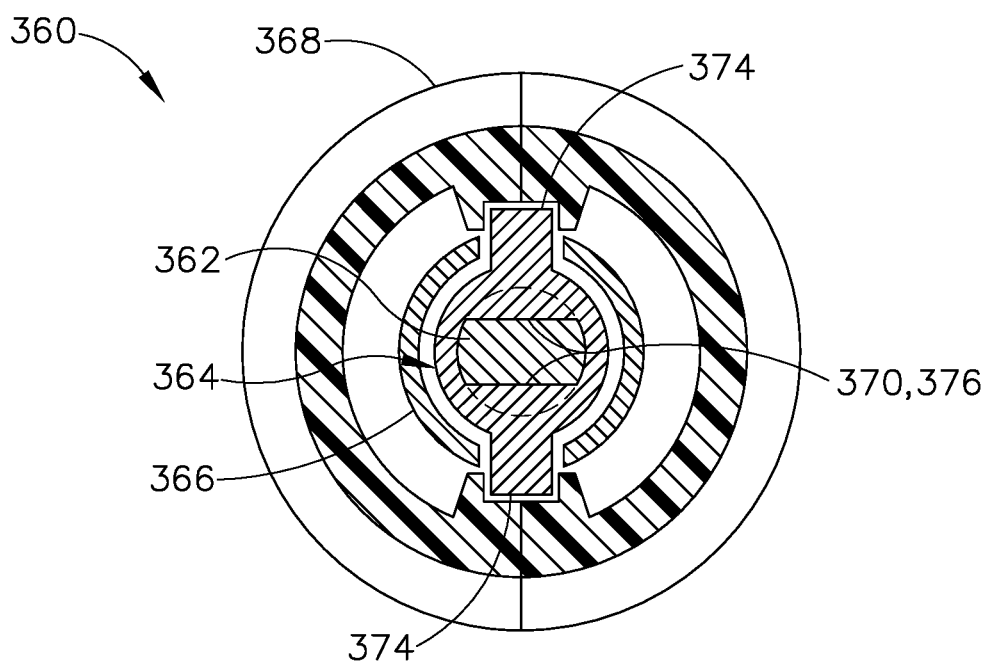
FIG. 40 depicts an end sectional view taken along section line 40-40 in FIG. 39, showing additional details of the shaft assembly, the rotation knob, and the torque transfer collar.

N. Exemplary Waveguide Having Slots with Planar Base Surfaces and Torque Transfer Collar Having Inner Radial Projections Received within Slots FIGS. 39 and 40 show an exemplary torque transfer assembly (360) suitable for use with ultrasonic surgical instrument (10). Torque transfer assembly (360) includes a waveguide (362), a torque transfer collar (364) encircling waveguide (362), a tube (366) enclosing waveguide (362), and a rotation knob (368) to which waveguide and tube (366) are coupled rotationally via torque transfer collar (364). In the present example, rotation knob (368) includes first and second knob halves configured to couple together to enclose waveguide (362), collar (364), and tube (366) therein. In some examples, tube (366) may be configured as an inner tube or an outer tube in combination with an additional tube (not shown). Further, it will be appreciated that in other examples only waveguide (362) and torque transfer collar (364) of assembly (360) may be incorporated into ultrasonic surgical instrument (10), with outer and inner tubes (34, 36) and rotation knob (46).

Waveguide (362) is similar to waveguide (40) described above in that a threaded proximal end (363) of waveguide (362) is configured to acoustically couple with ultrasonic transducer (26), and waveguide (362) is configured to communicate ultrasonic energy from transducer (26) to ultrasonic blade (28). A proximal portion of waveguide (362) includes a nodal coupling feature in the form of a pair of opposed slots (370) arranged at a proximal acoustic node of waveguide (362). Slots (370) are diametrically opposed from one another, and each slot (370) is configured as a "flat" that extends axially between closed proximal and distal ends to define a planar base surface, similar to slots (94) and base surfaces (96) described above in connection with FIGS. 10-12.

Torque transfer collar (364) includes an annular collar body (372) configured to encircle waveguide (362) at its proximal acoustic node, and a pair of tab-like lugs (374) extending axially and radially outwardly from collar body (372) at diametrically opposed positions. Lugs (374) are configured to secure collar (364) rotationally and axially relative to rotation knob (368), as well as rotationally relative to tube (366), in a manner similar to lugs (56) described above. An interior of collar (364) includes a pair of opposed projections (376) extending radially inwardly toward waveguide (362). Collar projections (376) are configured to be received within waveguide slots (370) and engage the planar base surfaces thereof to thereby fix torque transfer collar (364) rotationally relative to waveguide (362). Further, proximal and distal sides of each collar projection (376) are configured to abut the closed proximal and distal ends of the respective waveguide slot (370) to thereby fix torque transfer collar (364) axially relative to waveguide (362). In various examples, torque transfer collar (364) may be overmolded onto waveguide (362).

Figure 41:
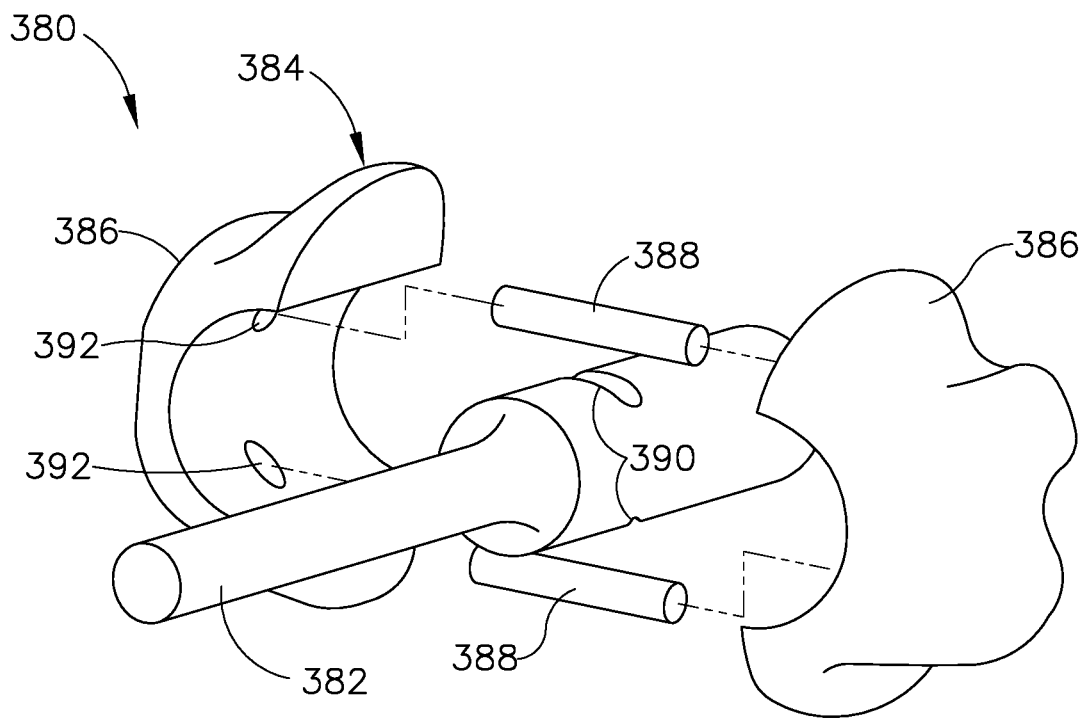
FIG. 41 depicts a disassembled perspective view of another exemplary waveguide, a rotation knob, and a torque transfer structure comprising first and second pins.
Figure 42:
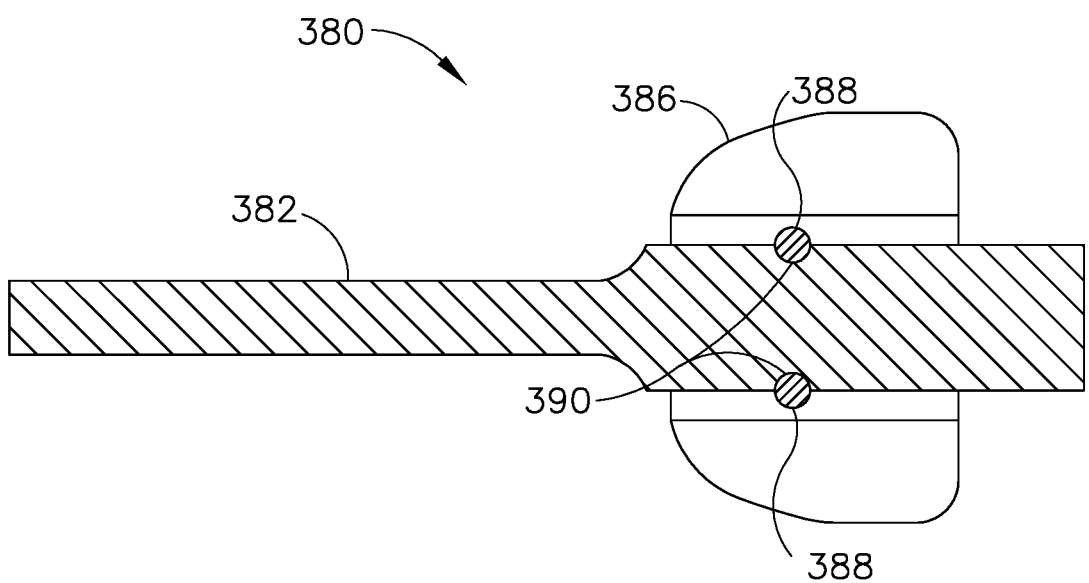
FIG. 42 depicts a side sectional view of the waveguide, the rotation knob, and the torque transfer pins of FIG. 41.

O. Exemplary Waveguide Having Transverse Slots and Torque Transfer Structure Comprising Elongate Transverse Members FIGS. 41 and 42 show an exemplary torque transfer assembly (380) suitable for use with ultrasonic surgical instrument (10). Torque transfer assembly (380) includes a waveguide (382), a rotation knob (384) having first and second knob halves (386) configured to couple together about waveguide (382), and a torque transfer structure configured to rotationally and axially fix waveguide (382) relative to rotation knob (384). The torque transfer structure of the present example is shown in the form of a pair of elongate pins (388) extending transversely relative to a central axis of waveguide (382). A proximal portion of waveguide (382) includes a nodal coupling feature in the form of a pair of opposed slots (390) arranged at a proximal acoustic node of waveguide (382). Slots (390) are diametrically opposed from one another, and each slot (390) is configured as a rounded notch extending transversely through waveguide (382) at an outer circumference thereof.

As shown best in FIG. 42, each slot (390) is configured to receive a circumferential portion of a respective transverse pin (388) such that opposed proximal and distal sides of slot (390) engage respective proximal and distal sides of pin (388). The lateral ends of each transverse pin (388) are received within sockets (392) formed in interiors of rotation knob (384), for example with an interference-fit engagement. Accordingly, waveguide (382) is fixed axially and rotationally relative to rotation knob (384) via engagement with transverse pins (388).

While the teachings herein are disclosed in connection an ultrasonic surgical instrument (10), it will be appreciated that they may also be employed in connection with surgical instruments configured to provide a combination of ultrasonic and radio frequency (RF) energies. Examples of such instruments and related methods and concepts are disclosed in U.S. Pat. No. 8,663,220, entitled "Ultrasonic Surgical Instruments," issued Mar. 4, 2014, the disclosure of which is incorporated by reference herein; U.S. Pub. No. 2015/0141981, entitled "Ultrasonic Surgical Instrument with Electrosurgical Feature," published May 21, 2015, issued as U.S. Pat. No. 9,949,785 on Apr. 24, 2018, the disclosure of which is incorporated by reference herein; and U.S. Pub. No. 2017/0000541, entitled "Surgical Instrument with User Adaptable Techniques," published Jan. 5, 2017, the disclosure of which is incorporated by reference herein.

II. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An ultrasonic surgical instrument, comprising: (a) a body; (b) a shaft extending distally from the body and defining a shaft axis; (c) an ultrasonic transducer supported by the body; (d) a waveguide coupled to the ultrasonic transducer and extending distally through the shaft, wherein the ultrasonic transducer is configured to drive the waveguide with ultrasonic energy; (e) an end effector coupled to a distal end of the shaft, wherein the waveguide is configured to communicate ultrasonic energy from the ultrasonic transducer to the end effector; (f) a rotation knob rotatably coupled to the body and configured to rotate the shaft, the waveguide, and the end effector together about the shaft axis relative to the body; and (g) a torque transfer structure positioned radially outwardly of and in direct contact with the waveguide at an acoustic node thereof, wherein the torque transfer structure is rotationally fixed relative to the waveguide and is configured to rotationally couple the waveguide with the shaft and the rotation knob, wherein the waveguide includes a first axial constraining feature defining a distally facing surface, and the torque transfer structure includes a second axial constraining feature defining a proximally facing surface, wherein the first and second axial constraining features are configured to engage such that the distally facing surface abuts the proximally facing surface to thereby constrain the waveguide axially relative to the torque transfer structure and the body.

Example 2

The ultrasonic surgical instrument of Example 1, wherein the torque transfer structure includes first and second transverse ends extending transversely relative to the shaft axis, wherein the transverse ends directly contact the rotation knob to thereby rotationally couple the torque transfer structure and the waveguide with the rotation knob.

Example 3

The ultrasonic surgical instrument of any one or more of the preceding Examples, wherein the torque transfer structure comprises a torque transfer collar encircling the waveguide at the acoustic node.

Example 4

The ultrasonic surgical instrument of Example 3, wherein the torque transfer collar includes first and second lugs extending radially outwardly therefrom, wherein the first and second lugs are configured to project radially through first and second lateral openings formed in the shaft and engage the rotation knob to thereby rotationally couple the waveguide and the shaft with the rotation knob.

Example 5

The ultrasonic surgical instrument of one or more of Examples 3 and 4, wherein the first axial constraining feature comprises a projection extending radially outwardly from the waveguide and defining the distally facing surface, wherein the torque transfer collar includes a slot formed in an interior thereof and configured to receive the projection.

Example 6

The ultrasonic surgical instrument of Example 5, wherein the torque transfer collar includes a snap member configured to couple to the projection with a snap-fit engagement.

Example 7

The ultrasonic surgical instrument of Example 6, wherein the snap member comprises a snap arm extending proximally from a proximal end of the torque transfer collar.

Example 8

The ultrasonic surgical instrument of any one or more of Examples 1 through 5, wherein the torque transfer collar comprises a fiber-reinforced composite structure having a plurality of fibers extending circumferentially about the waveguide.

Example 9

The ultrasonic surgical instrument of any one or more of Examples 1 through 5, wherein the projection comprises a circumferential projection extending radially outwardly from and circumferentially about the waveguide, wherein the slot comprises a circumferential slot formed in an interior of the torque transfer collar, wherein the circumferential slot is configured to receive the circumferential projection and defines the proximally facing surface.

Example 10

The ultrasonic surgical instrument of any one or more of Examples 5 through 7, wherein the torque transfer collar comprises proximal and distal components configured to interlock with one another to capture the projection therebetween, wherein the proximal component is configured to abut a proximal end of the projection, wherein the distal component defines the proximally facing surface and is configured to abut a distal end of the projection.

Example 11

The ultrasonic surgical instrument any one or more of Examples 3 through 5, wherein the first axial constraining feature comprises a spline projecting radially outwardly from the waveguide, wherein the second axial constraining feature comprises slot formed within an interior of the torque transfer collar, wherein a distal spline end of the spline is received within the slot and a proximal spline end of the spline extends proximally beyond the slot, wherein the distal spline end is formed with a first shape and the proximal spline end is formed with a second shape configured to interfere with the slot, wherein the second shape defines the distally facing surface.

Example 12

The ultrasonic surgical instrument of any one or more of Examples 3 through 5, wherein the first axial constraining feature comprises a spline projecting radially outwardly from the waveguide, wherein the second axial constraining feature comprises slot formed within an interior of the torque transfer collar, wherein a distal end of the spline is configured to engage a closed proximal end of the slot to limit proximal movement of the torque transfer collar relative to the waveguide, wherein the waveguide further includes a flange spaced distally from the projection and configured to engage a distal end of the torque transfer collar to limit distal movement of the torque transfer collar relative to the waveguide

Example 13

The ultrasonic surgical instrument of Example 3, wherein the first axial constraining feature comprises a slot provided by the waveguide and defining the distally facing surface, wherein the second axial constraining feature comprises a projection extending radially inwardly within an interior of the torque transfer collar and defining the proximally facing surface, wherein the slot is configured to receive the projection.

Example 14

The ultrasonic surgical instrument of Example 13, wherein the slot includes a planar surface and the projection is configured to abut the planar surface to thereby rotationally couple the torque transfer structure with the waveguide.

Example 15

The ultrasonic surgical instrument of Example 13, wherein the slot comprises a circumferential slot extending circumferentially about the waveguide, wherein the projection comprises a circumferential projection extending radially inwardly within an interior of the torque transfer collar, wherein the circumferential slot is configured to receive the circumferential projection.

Example 16

The ultrasonic surgical instrument of any one or more of Examples 1 and 2, wherein the torque transfer structure includes an elongate transverse member coupled to the rotation knob and extending transversely relative to the shaft axis, wherein the waveguide includes a slot extending transversely through an outer surface thereof at the acoustic node, wherein the elongate transverse member extends through the slot and thereby fixes the waveguide rotationally and axially relative to the rotation knob.

Example 17

An ultrasonic surgical instrument comprising: (a) a body; (b) a shaft extending distally from the body and defining a shaft axis; (c) an ultrasonic transducer supported by the body; (d) a waveguide coupled to the ultrasonic transducer and extending distally through the shaft, wherein the ultrasonic transducer is configured to drive the waveguide with ultrasonic energy, wherein the waveguide includes a plurality of projections extending radially outwardly therefrom at an acoustic node of the waveguide; (e) an end effector coupled to a distal end of the shaft, wherein the waveguide is configured to communicate ultrasonic energy from the ultrasonic transducer to the end effector; (f) a rotation knob rotatably coupled to the body and configured to rotate the shaft, the waveguide, and the end effector together about the shaft axis relative to the body; and (g) a torque transfer collar encircling the waveguide at the acoustic node and configured to rotationally couple the waveguide with the shaft and the rotation knob, wherein the torque transfer collar includes a plurality of slots configured to receive the projections to thereby rotationally fix the waveguide relative to the torque transfer collar, wherein the torque transfer collar is configured to abut a first radially extending portion of the waveguide to limit distal movement of the waveguide relative to the torque transfer collar, wherein the torque transfer collar is configured to abut a second radially extending portion of the waveguide to limit proximal movement of the waveguide relative to the torque transfer collar, wherein the first and second radially extending portions are spaced axially from one another.

Example 18

The ultrasonic surgical instrument of Example 17, wherein the projections define the first radially extending portion of the waveguide, wherein the waveguide includes a flange arranged distally of the projections and defining the second radially extending portion.

Example 19

An ultrasonic surgical instrument comprising: (a) a body; (b) a shaft extending distally from the body and defining a shaft axis; (c) an ultrasonic transducer supported by the body; (d) a waveguide coupled to the ultrasonic transducer and extending distally through the shaft, wherein the ultrasonic transducer is configured to drive the waveguide with ultrasonic energy; (e) an end effector coupled to a distal end of the shaft, wherein the waveguide is configured to communicate ultrasonic energy from the ultrasonic transducer to the end effector; (f) a rotation knob rotatably coupled to the body and configured to rotate the shaft, the waveguide, and the end effector together about the shaft axis relative to the body; and (g) a torque transfer collar encircling the waveguide at an acoustic node thereof, wherein the torque transfer collar is configured to rotationally couple the waveguide with the shaft and the rotation knob, wherein the torque transfer collar includes a first collar component and a second collar component configured to couple together about the waveguide and thereby constrain the waveguide axially relative to the torque transfer collar.

Example 20

The ultrasonic surgical instrument of Example 19, wherein the waveguide includes a projection, wherein the first collar component comprises a proximal component and the second collar component comprises a distal component, wherein the proximal and distal components are configured to mate together to capture the projection therebetween.

III. MISCELLANEOUS

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; U.S. Pat. No. 8,844,789, entitled "Automated End Effector Component Reloading System for Use with a Robotic System," issued Sep. 30, 2014, the disclosure of which is incorporated by reference herein; U.S. Pat. No. 8,820,605, entitled "Robotically-Controlled Surgical Instruments," issued Sep. 2, 2014, the disclosure of which is incorporated by reference herein; U.S. Pat. No. 8,616,431, entitled "Shiftable Drive Interface for Robotically-Controlled Surgical Tool," issued Dec. 31, 2013, the disclosure of which is incorporated by reference herein; U.S. Pat. No. 8,573,461, entitled "Surgical Stapling Instruments with Cam-Driven Staple Deployment Arrangements," issued Nov. 5, 2013, the disclosure of which is incorporated by reference herein; U.S. Pat. No. 8,602,288, entitled "Robotically-Controlled Motorized Surgical End Effector System with Rotary Actuated Closure Systems Having Variable Actuation Speeds," issued Dec. 10, 2013, the disclosure of which is incorporated by reference herein; U.S. Pat. No. 9,301,759, entitled "Robotically-Controlled Surgical Instrument with Selectively Articulatable End Effector," issued Apr. 5, 2016, the disclosure of which is incorporated by reference herein; U.S. Pat. No. 8,783,541, entitled "Robotically-Controlled Surgical End Effector System," issued Jul. 22, 2014, the disclosure of which is incorporated by reference herein; U.S. Pat. No. 8,479,969, entitled "Drive Interface for Operably Coupling a Manipulatable Surgical Tool to a Robot," issued Jul. 9, 2013; U.S. Pat. No. 8,800,838, entitled "Robotically-Controlled Cable-Based Surgical End Effectors," issued Aug. 12, 2014, the disclosure of which is incorporated by reference herein; and/or U.S. Pat. No. 8,573,465, entitled "Robotically-Controlled Surgical End Effector System with Rotary Actuated Closure Systems," issued Nov. 5, 2013, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An ultrasonic surgical instrument, comprising:
   (a) a body;
   (b) a shaft extending distally from the body and defining a shaft axis;
   (c) an ultrasonic transducer supported by the body;
   (d) a waveguide coupled to the ultrasonic transducer and extending distally through the shaft, wherein the ultrasonic transducer is configured to drive the waveguide with ultrasonic energy;
   (e) an end effector coupled to a distal end of the shaft, wherein the waveguide is configured to communicate ultrasonic energy from the ultrasonic transducer to the end effector;
   (f) a rotation knob rotatably coupled to the body and configured to rotate the shaft, the waveguide, and the end effector together about the shaft axis relative to the body; and
   (g) a torque transfer structure positioned radially outwardly of and in direct contact with the waveguide at an acoustic node thereof, wherein the torque transfer structure is rotationally fixed relative to the waveguide and is configured to rotationally couple the waveguide with the shaft and the rotation knob, wherein the torque transfer structure includes first and second lugs extending transversely from the torque transfer structure relative to the shaft axis, wherein each of the first and second lugs engage the rotation knob to thereby rotationally couple the waveguide and the shaft with the rotation knob, wherein the waveguide includes a first axial constraining feature defining a distally facing surface, and the torque transfer structure includes a second axial constraining feature defining a proximally facing surface, wherein the first and second axial constraining features are configured to engage such that the distally facing surface abuts the proximally facing surface to thereby constrain the waveguide axially relative to the torque transfer structure and the body.

2. The ultrasonic surgical instrument of claim 1, wherein the first and second lugs directly contact the rotation knob to thereby rotationally couple the torque transfer structure and the waveguide with the rotation knob.

3. The ultrasonic surgical instrument of claim 1, wherein the torque transfer structure comprises a torque transfer collar encircling the waveguide at the acoustic node.

4. The ultrasonic surgical instrument of claim 3, wherein the torque transfer collar includes the first and second lugs extending radially outwardly therefrom, wherein the first and second lugs are configured to project radially through first and second lateral openings formed in the shaft and engage the rotation knob to thereby rotationally couple the waveguide and the shaft with the rotation knob.

5. The ultrasonic surgical instrument of claim 3, wherein the first axial constraining feature comprises a projection extending radially outwardly from the waveguide and defining the distally facing surface, wherein the torque transfer collar includes a slot formed in an interior thereof and configured to receive the projection.

6. The ultrasonic surgical instrument of claim 5, wherein the torque transfer collar includes a snap member configured to couple to the projection with a snap-fit engagement.

7. The ultrasonic surgical instrument of claim 6, wherein the snap member comprises a snap arm extending proximally from a proximal end of the torque transfer collar.

8. An ultrasonic surgical instrument, comprising:
(a) a body;
(b) a shaft extending distally from the body and defining a shaft axis;
(c) an ultrasonic transducer supported by the body;
(d) a waveguide coupled to the ultrasonic transducer and extending distally through the shaft, wherein the ultrasonic transducer is configured to drive the waveguide with ultrasonic energy, wherein the waveguide includes a waveguide body and a plurality of projections, wherein the waveguide body longitudinally extends along the shaft axis and each of the projections extends radially outwardly from the waveguide body at an acoustic node of the waveguide, wherein the projections are spaced apart from the shaft axis and integrally formed with the waveguide body;
(e) an end effector coupled to a distal end of the shaft, wherein the waveguide is configured to communicate ultrasonic energy from the ultrasonic transducer to the end effector;
(f) a rotation knob rotatably coupled to the body and configured to rotate the shaft, the waveguide, and the end effector together about the shaft axis relative to the body; and
(g) a torque transfer collar encircling the waveguide at the acoustic node and configured to rotationally couple the waveguide with the shaft, and the rotation knob, wherein the torque transfer collar includes a plurality of slots configured to receive the projections to thereby rotationally fix the waveguide relative to the torque transfer collar, wherein the torque transfer collar is configured to abut a first radially extending portion of the waveguide to limit distal movement of the waveguide relative to the torque transfer collar, wherein the torque transfer collar is configured to abut a second radially extending portion of the waveguide to limit proximal movement of the waveguide relative to the torque transfer collar, wherein the first and second radially extending portions are spaced axially from one another, wherein the torque transfer collar includes a first lug extending radially outward therefrom, and wherein the first lug is configured to transfer torque from the rotational knob to the waveguide.

9. The ultrasonic surgical instrument of claim 8, wherein the projections define the first radially extending portion of the waveguide, wherein the waveguide includes a flange arranged distally of the projections and defining the second radially extending portion.

10. The ultrasonic surgical instrument of claim 8, wherein the plurality of slots longitudinally extends and are configured to longitudinally receive the plurality of projections, respectively.

11. The ultrasonic surgical instrument of claim 10, wherein the torque transfer collar includes a second lug extending radially outwardly therefrom, and wherein the second lug is configured to transfer torque from the rotational knob to the waveguide.

12. The ultrasonic surgical instrument of claim 8, wherein the torque transfer structure includes a proximally located snap arm configured to limit distal movement of the torque transfer structure relative to the waveguide.

13. The ultrasonic surgical instrument of claim 8, wherein the torque transfer collar includes a second lug extending radially outwardly therefrom, and wherein the second lug is configured to transfer torque from the rotational knob to the waveguide.

14. An ultrasonic surgical instrument, comprising:
(a) a body;
(b) a shaft extending distally and longitudinally from the body and defining a shaft axis;
(c) an ultrasonic transducer supported by the body;
(d) a waveguide coupled to the ultrasonic transducer and extending distally through the shaft, wherein the ultrasonic transducer is configured to drive the waveguide with ultrasonic energy, wherein the waveguide includes an acoustic node and a projection, wherein the projection is positioned at the acoustic node and transversely projects therefrom;
(e) an end effector coupled to a distal end of the shaft, wherein the waveguide is configured to communicate ultrasonic energy from the ultrasonic transducer to the end effector;
a rotation knob rotatably coupled to the body and configured to rotate the shaft, the waveguide, and the end effector together about the shaft axis relative to the body; and
(g) a torque transfer structure including an interior surface and an exterior surface positioned such that the exterior surface is radially outward relative to the interior surface, wherein the torque transfer structure further defines a slot radially extending from the interior surface toward the exterior surface and terminating radially inward of the exterior surface, wherein the slot of the torque transfer structure longitudinally extends and is configured to longitudinally receive the projection of the waveguide such that the torque transfer structure is in direct contact with the waveguide at the acoustic node thereof and the torque transfer structure is rotationally fixed relative to the waveguide, and wherein the torque transfer structure is configured to rotationally couple the waveguide with the shaft and the rotation knob wherein the projection is a spline having a distal end, wherein the distal end of the spline is configured to engage a closed distal end of the slot to limit proximal movement of the torque transfer structure relative to the waveguide, wherein the torque transfer structure includes a proximally located snap arm configured to limit distal movement of the torque transfer structure relative to the waveguide.

\* \* \* \* \*

UNITED STATES PATENT AND TRADEMARK OFFICE
CERTIFICATE OF CORRECTION

Page 1 of 1

PATENT NO. : 10,813,662 B2
APPLICATION NO. : 15/644930
DATED : October 27, 2020
INVENTOR(S) : Rafael J. Ruiz Ortiz et al.

It is certified that error appears in the above-identified patent and that said Letters Patent is hereby corrected as shown below:

In the Claims

Column 30, Claim 14, Line 57, reads "a rotation knob rotatably coupled to the body and..."; which should be deleted and replaced with "(f) a rotation knob rotatably coupled to the body and..."

Signed and Sealed this
Twelfth Day of January, 2021

Andrei Iancu
*Director of the United States Patent and Trademark Office*